(12) United States Patent
Amano

(10) Patent No.: US 6,432,060 B1
(45) Date of Patent: Aug. 13, 2002

(54) BLOOD PRESSURE MONITOR AND PULSE WAVE DETECTION APPARATUS

(75) Inventor: Kazuhiko Amano, Yokohama (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 09/673,734
(22) PCT Filed: Feb. 22, 2000
(86) PCT No.: PCT/JP00/00997
§ 371 (c)(1),
(2), (4) Date: Oct. 19, 2000
(87) PCT Pub. No.: WO00/49943
PCT Pub. Date: Aug. 31, 2000

(30) Foreign Application Priority Data

Feb. 22, 1999 (JP) .............................. 11-043451

(51) Int. Cl.$^7$ ................................. A61B 5/02
(52) U.S. Cl. .................... 600/490; 600/485; 600/500
(58) Field of Search ................ 600/485, 490, 600/500, 501, 502, 503

(56) References Cited

U.S. PATENT DOCUMENTS

| | | | | |
|---|---|---|---|---|
| 4,951,679 A | * | 8/1990 | Harada ........................ | 600/485 |
| 6,132,382 A | * | 10/2000 | Archibald et al. ........... | 600/485 |
| 6,132,383 A | * | 10/2000 | Chesney et al. ............. | 600/502 |

FOREIGN PATENT DOCUMENTS

| | | |
|---|---|---|
| JP | 01265941 A | 10/1989 |
| JP | 05-300885 | 11/1993 |
| JP | 08187229 A | 7/1996 |
| JP | 08332171 A | 12/1996 |
| JP | 2804484 | 7/1998 |
| JP | 10295657 A | 11/1998 |
| JP | 10314132 A | 12/1998 |

* cited by examiner

Primary Examiner—Kevin Shaver
Assistant Examiner—Patricia Mallari
(74) Attorney, Agent, or Firm—Michael T. Gabrik

(57) ABSTRACT

The blood pressure monitor (10) comprises an artery pressing section which locally presses an artery of the extremities or fingers at an arbitrarily variable pressing force, a vibration sensor (22) detecting a vibration of the artery at the pressed point or points on a peripheral side thereof, a mounting mechanism (26) which positions the artery pressing section and the vibration sensor (22) on the artery, a blood pressure determination section which determines the maximum and minimum pressures based on various pressing force values applied by the above-mentioned artery pressing section and signals detected by the vibration sensor (22) at these various pressing force values, guides (34) which are provided on each side of the vibration sensor (22) and guide the vibration sensor (22) to the artery by being located on the both sides of the artery, and a peripheral side pressing section which presses the artery on the peripheral side from the vibration sensor (22).

The blood pressure monitor (10) does not impart an unpleasant or disagreeable feeling to the subject.

29 Claims, 24 Drawing Sheets

BLOOD PRESSURE MONITOR AND PULSE WAVE DETECTION APPARATUS

TECHNICAL FIELD

The present invention relates to a blood pressure monitor and pulse wave detection apparatus.

BACKGROUND OF THE ART

Blood pressure is commonly measured by auscultation which consists of applying a pressing force greater than the maximum blood pressure to the artery by pressing the brachium or wrist around the circumference and detecting a vibration of the pressed artery on the peripheral side, while gradually decreasing the pressing force.

A blood pressure monitor disclosed in Japanese Patent No. 2804484, for example, has a means of detecting displacement of the cuff for applying pressure around the wrist.

Japanese Patent Application Laid-open No. 5-300885 discloses a blood pressure monitor designed as shown in FIG. 2 of the published document, wherein the arterial blood flow is controlled by the pressing force applied to the arm by altering the degree of expansion of an air bag 7 which consists of section of a cuff wound around the arm. This pressing force is monitored by a third pressure sensor 1, which latches the pressing force when a first pressure sensor 2 detects the maximum arterial pulse wave and the pressing force when a second pressure sensor 3 detects an arterial pulse wave above a prescribed level. The peripheral blood pressure is determined based on the latched pressure information.

In these blood pressure measuring methods, however, almost the entire circumference of the brachium or wrist is pressed so that the nervous tissues which are distributed densely close to funny bones in the case of the wrist, for instance, are pressed, imparting an unpleasant and disagreeable feeling. Such an unpleasant and disagreeable feeling caused by pressing the entire circumference of the measuring section such as the extremities and fingers has been experienced when the blood pressure is measured by pressing the entire circumference of other parts such as brachium and fingers.

DISCLOSURE OF THE INVENTION

The present invention has been completed in view of this situation and has an object of providing a blood pressure monitor and a pulse wave detection apparatus which impart an unpleasant and disagreeable feeling to a subject only to a minimal degree.

One aspect of the present invention provides a blood pressure monitor comprising:

an artery pressing section which locally presses an artery of any one of extremities and fingers at an arbitrarily variable pressing force;

a control section which controls the pressing force applied by the artery pressing section;

a vibration sensor detecting a vibration of the artery at a point pressed by the artery pressing section or at a point peripheral to the point pressed by the artery pressing section; and a blood pressure determination section which determines a maximum blood pressure and a minimum blood pressure based on various pressing force values applied by the artery pressing section and signals detected by the vibration sensor at the various pressing force values.

In this blood pressure monitor, the blood pressure determination section determines the maximum and minimum pressures based on various pressing force values applied when the artery pressing section locally presses an artery of the extremities or fingers and the signals detected by the vibration sensor at these various pressing force values. Because the extremities or fingers are not pressed over the entire circumference, no discomfort or unfavorable feeling will be imparted to the subject.

In addition, because the artery pressing section presses the artery only locally, the pressing operation will not be interfered with by the sinews or bones which may be present close to the artery. Therefore, the pressing operation can press the artery with certainty, ensuring measurement of the blood pressure more accurately than in the conventional method in which the entire circumference of the extremities or fingers is pressed by a cuff or the like.

Another aspect of the present invention provides a blood pressure monitor comprising:

a first artery pressing section which locally presses a first artery of any one of extremities and fingers having the first artery and a second artery at an arbitrarily variable pressing force;

a control section which controls the pressing force applied by the first artery pressing section;

a second artery pressing section which locally presses the second artery;

a vibration sensor detecting a vibration of the first artery at a pressed point or on a peripheral side thereof; and a blood pressure determination section which determines a maximum blood pressure and a minimum blood pressure based on various pressing force values applied by the first artery pressing section and a signal detected by the vibration sensor at each of the pressing force values.

In this blood pressure monitor, the blood pressure determination section determines the maximum and minimum pressures based on various pressing force values applied when the first artery pressing section locally presses an artery of the extremities or fingers and the signals detected by the vibration sensor at these various pressing force values. Because the extremities or fingers are not pressed over the entire circumference, no discomfort or unfavorable feeling will be imparted to the subject.

In addition, because this blood pressure monitor is equipped with the second artery pressing section which locally presses the second artery, the monitor can shut off the blood flow to the peripheral side from the pressed point. Therefore, the vibration of the first artery detected by the vibration sensor will not be affected by the pulses due to the blood flowing from the second artery via the artery which connect the second and first arteries, thereby ensuring more accurate blood pressure measurement.

The above-mentioned blood pressure monitor may further comprise a positioning mechanism which positions the first pressing section and the vibration sensor on the artery.

Such a positioning mechanism ensures easy determination of positioning for the artery pressing section and the vibration sensor on the artery.

The above-mentioned blood pressure monitor may further comprise guides provided on each side of the vibration sensor and guiding the vibration sensor to the artery by being located on both sides of the artery.

This configuration ensures easy and certain positioning of the vibration sensor on the artery by causing the guides which guide the vibration sensor on the artery to be located on each side of the artery.

The above-mentioned blood pressure monitor may further comprise a peripheral side pressing section which presses the artery at a point peripheral to the vibration sensor and almost completely shuts off the vibration transmitted by an artery section peripheral to the vibration sensor.

According to this configuration, because the artery is pressed by the peripheral side pressing section on the peripheral side from the artery pressing section and the vibration sensor, pulses transmitted from branch passages of arteries or the like can be shut off, enabling mere accurate blood pressure measurement.

In the above-mentioned blood pressure monitor, it is preferable that the vibration sensor detects the vibration transmitted to the artery pressing section.

The blood pressure can be measured without causing the oscillatory sensor to directly come into contact with the skin.

The above-mentioned blood pressure monitor may further comprise a sensor pressing section which causes the vibration sensor to press the artery.

This configuration, which enables the sensor pressing section of the vibration sensor to press the artery, causes the vibration sensor to press the artery at an appropriate pressure so that a vibration from the artery can be detected with certainty.

In the above-mentioned blood pressure monitor, the vibration sensor may be a pulse wave sensor detecting a pulse waveform, and the blood pressure monitor may further comprise a conversion section which converts the pulse waveform into a blood pressure waveform based on the maximum blood pressure and the minimum blood pressure.

In this blood pressure monitor, the conversion section converts the pulse waveforms obtained from a pulse wave detection apparatus located on the artery into blood pressure waveforms based on the maximum and minimum blood pressures measured by the blood pressure monitor, thereby obtaining blood pressure waveforms. Therefore, blood pressure waveforms can be obtained non-invasively.

The above-mentioned blood pressure monitor may further comprise a blood-pressure-waveform processing section which calculates at least one of following items based on the blood pressure waveform obtained by the conversion section; a mean blood pressure, a pulse pressure which is a difference between the maximum blood pressure and the minimum blood pressure, a after-ejection pressure which is a pressure difference between a dicrotic notch and the maximum blood pressure, a dicrotic wave height which is a pressure difference between the dicrotic notch and a dicrotic wave peak, an after-ejection pressure ratio which is the after-ejection pressure normalized by the pulse pressure, a dicrotic wave height ratio which is the dicrotic wave height normalized by the pulse pressure, and a dicrotic wave height after-ejection pressure ratio which is a ratio of the dicrotic wave height and the after-ejection pressure.

In this manner, at least one of the mean blood pressure, pulse pressure which is the difference between the maximum and minimum blood pressures, after-ejection pressure which is the pressure difference between a dicrotic notch and the maximum blood pressure, dicrotic wave height which is the pressure difference between the dicrotic notch and the dicrotic wave peak, after-ejection pressure ratio which is the after-ejection pressure normalized by the pulse pressure, and dicrotic wave height after-ejection pressure ratio which is a ratio of the dicrotic wave height and the after-ejection pressure can be calculated by the blood-pressure-waveform processing section.

In the above-mentioned blood pressure monitor, the artery pressed by the artery pressing section, of which vibration is detected by the vibration sensor, may be a radial artery.

Because the blood pressure monitor can measure blood pressure without pressing section of the wrist around the ulna in which many nerve tissues are present, it is possible to measure the blood pressure on the wrist without imparting an unpleasant and disagreeable feeling to a subject.

A pulse wave detection apparatus which is further aspect of the present invention comprises:

an artery pressing section which locally presses an artery of any one of extremities and fingers at an arbitrarily variable pressing force;

a control section which controls the pressing force applied by the artery pressing section; and a pulse sensor detecting pulse of the artery at a pressed point or on a peripheral side thereof.

In this pulse wave detection apparatus, the pulse wave sensor detects pulse waves at the point of the artery pressing section or on the peripheral side based on variable pressing force values applied when the artery pressing section locally presses the artery of the extremities or fingers. Therefore, pulse waves at various pressures applied by the artery pressing section can be detected.

The above-mentioned pulse wave detection apparatus may further comprise a positioning mechanism which positions the artery pressing section and the pulse sensor on the artery.

Such a positioning mechanism ensures easy determination of positioning for the artery pressing section and the vibration sensor on the artery.

The above-mentioned pulse wave detection apparatus may further comprise guides provided on each side of the pulse sensor and guiding the pulse sensor to the artery by being located on both sides of the artery.

This configuration ensures easy and certain positioning of the pulse detector on the artery by causing the guides which guide the pulse detector on the artery to be located on each side of the artery.

In the above-mentioned pulse wave detection apparatus, the pulse sensor may detect the vibration transmitted to the artery pressing section.

This configuration enables the pulse detector to detect pulse waves without applying pressure to the artery from above the skin.

The above-mentioned pulse wave detection apparatus may further comprise a sensor pressing section which causes the pulse sensor to press the artery.

This configuration, which enables the sensor pressing section of the pulse detector to press the artery, causes the pulse detector to press the artery at an appropriate pressure so that pulses from the artery can be detected with certainty.

In the above-mentioned pulse wave detection apparatus, the artery pressed by the artery pressing section, of which pulse is detected by the pulse sensor, may be a radial artery.

Therefore, pulse waves from the radial artery at various pressures applied by the artery pressing section can be detected The above-mentioned pulse wave detection apparatus may further comprise:

a pressure waveform processing section which calculates at least one of the following items based on the pulse waveform obtained by the pulse sensor:

an after-ejection pressure ratio which is an after-ejection pressure normalized by a pulse pressure, the after-ejection pressure being a pressure difference between a dicrotic notch and a maximum blood pressure, the pulse pressure being a difference between the maximum blood pressure and a minimum blood pressure;

a dicrotic notch difference ratio which is a dicrotic notch difference normalized by the pulse pressure, the dicrotic notch difference being a difference between a blood pressure of the dicrotic notch and the minimum blood pressure;

a mean-blood-pressure pulse-pressure ratio which is a ratio of the mean-blood-pressure and the pulse pressure, a dicrotic wave height ratio which is a dicrotic wave height normalized by the pulse pressure; and a dicrotic-wave-height after-ejection pressure ratio which is a ratio of the dicrotic wave height and the after-ejection pressure.

A still further aspect of the present invention provides a blood pressure monitor comprising:

a band wound around any one of extremities and fingers;

a pressure applying section which is installed on a inner surface of the band and applies a variable pressure around any one of the extremities and fingers by changing a volume of a fluid included therein;

an artery pressing section which is attached to the pressure applying section and locally presses an artery of any one of the extremities and fingers;

a control section which controls a pressing force applied to the artery by the artery pressing section by changing the pressure applied by the pressure applying section;

a pressure sensor which detects a vibration of the artery transmitted as a pressure change of the fluid, the vibration transmitted to the fluid via the artery pressing section and the pressure applying section; and a blood pressure determination section which determines a maximum blood pressure and a minimum blood pressure based on various pressing force values applied by the artery pressing section and a signal detected by the pressure sensor at each of the pressing force values.

In this blood pressure monitor, the artery pressing section installed in the pressure applying section located inside the band locally presses the artery at various pressures. The blood pressure determination section determines the maximum and minimum pressures based on the various pressing force values applied and the signals detected by the pressure sensor at these various pressing force values. Therefore, the artery is pressed by the artery pressing section at a sufficient pressure so that the region in which the pressure applying section or the band come into contact may not become so large. As a result, a pressure sufficiently great as to impart an unpleasant or disagreeable feeling to the subject will not be applied.

In addition, because the artery pressing section presses the artery only locally, the pressing operation will not be interfered with by the sinews or bones which may be present close to the artery. Therefore, the pressing operation can press the artery with certainty, ensuring measurement of the blood pressure more accurately than in the conventional method in which the artery is directly pressed by a cuff or the like applied to the circumference of the extremities or fingers Thus, more accurate blood pressure measurement can be ensured.

A still further aspect of the present invention provides a blood pressure monitor comprising:

a band wound around any one of extremities and fingers having a first artery and a second artery;

a pressure applying section which is installed on a inner surface of the band and applies a variable pressing force to the first artery by changing a volume of a fluid included therein;

a second artery pressing section which is attached to the pressure applying section and locally presses the second artery;

a control section which controls the pressure applied by the pressure applying section;

a pressure sensor which detects a vibration of the artery transmitted as a pressure change of the fluid via the pressure applying section; and a blood pressure determination section which determines a maximum blood pressure and a minimum blood pressure based on various pressing force values applied by the pressure applying section and a signal detected by the pressure sensor at each of the pressing force values.

Because this blood pressure monitor is equipped with the second artery pressing section which locally presses the second artery, the monitor can shut off the blood flow to the peripheral side from the pressed point. Therefore, the signals from the first artery detected by the pressure sensor will not be affected by the pulses due to the blood flowing from the second artery via the artery which connect the second and first arteries, thereby ensuring more accurate blood pressure measurement.

In addition, because the second artery pressing section locally presses the second artery, there will be no risk of nerves or the like around the second artery being strongly pressed, thus minimizing any unpleasant or disagreeable feeling imparted to the subject.

A still further aspect of the present invention provides a blood pressure monitor comprising:

a band wound around any one of extremities and fingers having a first artery and a second artery;

a first artery pressing section which is installed on a inner surface of the band and locally applies a variable pressing force to the first artery by changing a volume of a fluid included therein;

a second artery pressing section which is installed on a inner surface of the band and locally applies a variable pressing force to the second artery by changing a volume of a fluid included therein;

a control section which controls the pressing force applied by the first artery pressing section;

a pressure sensor which detects a vibration of the artery transmitted as a pressure change of the fluid via the first artery pressing section; and a blood pressure determination section which determines a maximum blood pressure and a minimum blood pressure based on various pressing force values applied by the first artery pressing section and a signal detected by the pressure sensor at each of the pressing force values.

In this blood pressure monitor, the first artery pressing section installed in the band locally presses the first artery at various pressures. The blood pressure determination section determines the maximum and minimum pressures based on the various pressing force values applied and the signals detected by the pressure sensor at these various pressing force values. Because the extremities or fingers are not pressed over the entire circumference by the first artery pressing section, no discomfort or unfavorable feeling will be imparted to the subject.

In addition, because this blood pressure monitor is equipped with the second artery pressing section which locally presses the second artery, the monitor can shut off the blood flow to the peripheral side from the pressed point. Therefore, the vibration from the first artery detected by the pressure sensor will not be affected by the pulses due to the blood flowing from the second artery via the artery which connect the second and first arteries, thereby ensuring more accurate blood pressure measurement.

A still further aspect of the present invention provides a blood pressure monitor comprising:

an artery pressing section which presses an artery of any one of extremities or fingers at an arbitrarily variable pressing force;

a control section which controls the pressing force applied to the artery by the artery pressing section so as to gradually increase the pressing force from a predetermined minimum pressing force;

a pressure sensor detecting a vibration of the artery at a point pressed by the artery pressing section or at a point peripheral to the point pressed by the artery pressing section; and a blood pressure determination section which determines a maximum blood pressure and a minimum blood pressure based on various pressing force values applied by the artery pressing section and a signal detected by the pressure sensor at each of the pressing force values.

According to this blood pressure monitor, the control section controls the pressure applied to the artery by the artery pressing section so that this pressure may be gradually increased from the prescribed minimum pressure. The blood pressure is measured based on the signals detected by the pressure sensor and the pressure applied at the point of measurement. The blood pressure is determined according to the same principle of the auscultation method using this blood pressure monitor. Specifically, a vibration of blood vessel walls due to blood flowing through the blood vessel constricted by the pressure applied on the peripheral side of the artery is monitored while changing the pressure applied by the artery. The blood pressure is then determined from the highest pressure of the artery pressing section detected by the vibration sensor which detects a vibration of the blood flowing through the constricted blood vessels as the maximum blood pressure, and the lowest pressure of the artery pressing section detected by the vibration sensor which detects a vibration of the blood flowing through the constricted blood vessels as the minimum blood pressure. In the blood pressure measurement using this blood pressure monitor, because the pressure applied by the pressure applying section is gradually increased starting from a pressure lower than the conceivable lowest pressure (the prescribed minimum value), the pressure measurement operation is completed when the pressure of the artery pressing section becomes almost equivalent to a pressure corresponding the maximum pressure. Therefore, the maximum pressure applied to the artery pressing section can be decreased using this blood pressure monitor as compared with conventional blood pressure monitors in which a pressure higher than the conceivable maximum pressure is first applied and then gradually decreased. As a result, a pressure sufficiently great as to impart an unpleasant or disagreeable feeling to the subject will not be applied.

The above-mentioned blood pressure monitor may further comprise a conversion section which converts a signal detected by the pressure sensor into a blood pressure waveform based on the maximum blood pressure and the minimum blood pressure.

In the blood pressure monitor, the blood pressure waveforms can be obtained from the conversion section which converts the signals detected by the pressure sensor based on the maximum and minimum blood pressure. Therefore, blood pressure waveforms can be obtained non-invasively.

The above-mentioned blood pressure monitor may further comprise a blood-pressure-waveform processing section which calculates at least one of following items based on the blood pressure waveform obtained by the conversion section: a mean blood pressure, a pulse pressure which is a difference between the maximum blood pressure and the minimum blood pressure, an after-ejection pressure which is a pressure difference between a dicrotic notch and the maximum blood pressure, a dicrotic wave height which is a pressure difference between the dicrotic notch and a dicrotic wave peak, an after-ejection pressure ratio which is the after-ejection pressure normalized by the pulse pressure, a dicrotic wave height ratio which is the dicrotic wave height normalized by the pulse pressure, and a dicrotic wave height after-ejection pressure ratio which is a ratio of the dicrotic wave height and the after-ejection pressure.

In this manner, at least one of the mean blood pressure, pulse pressure which is the difference between the maximum and minimum blood pressures, after-ejection pressure which is the pressure difference between a dicrotic notch and the maximum blood pressure, dicrotic wave height which is the pressure difference between the dicrotic notch and the dicrotic wave peak, after-ejection pressure ratio which is the after-ejection pressure normalized by the pulse pressure, and dicrotic wave height after-ejection pressure ratio which is a ratio of the is dicrotic wave height and the after-ejection pressure can be calculated by the blood-pressure-waveform processing section.

BEST MODE FOR CARRYING OUT THE INVENTION

Figure 1:
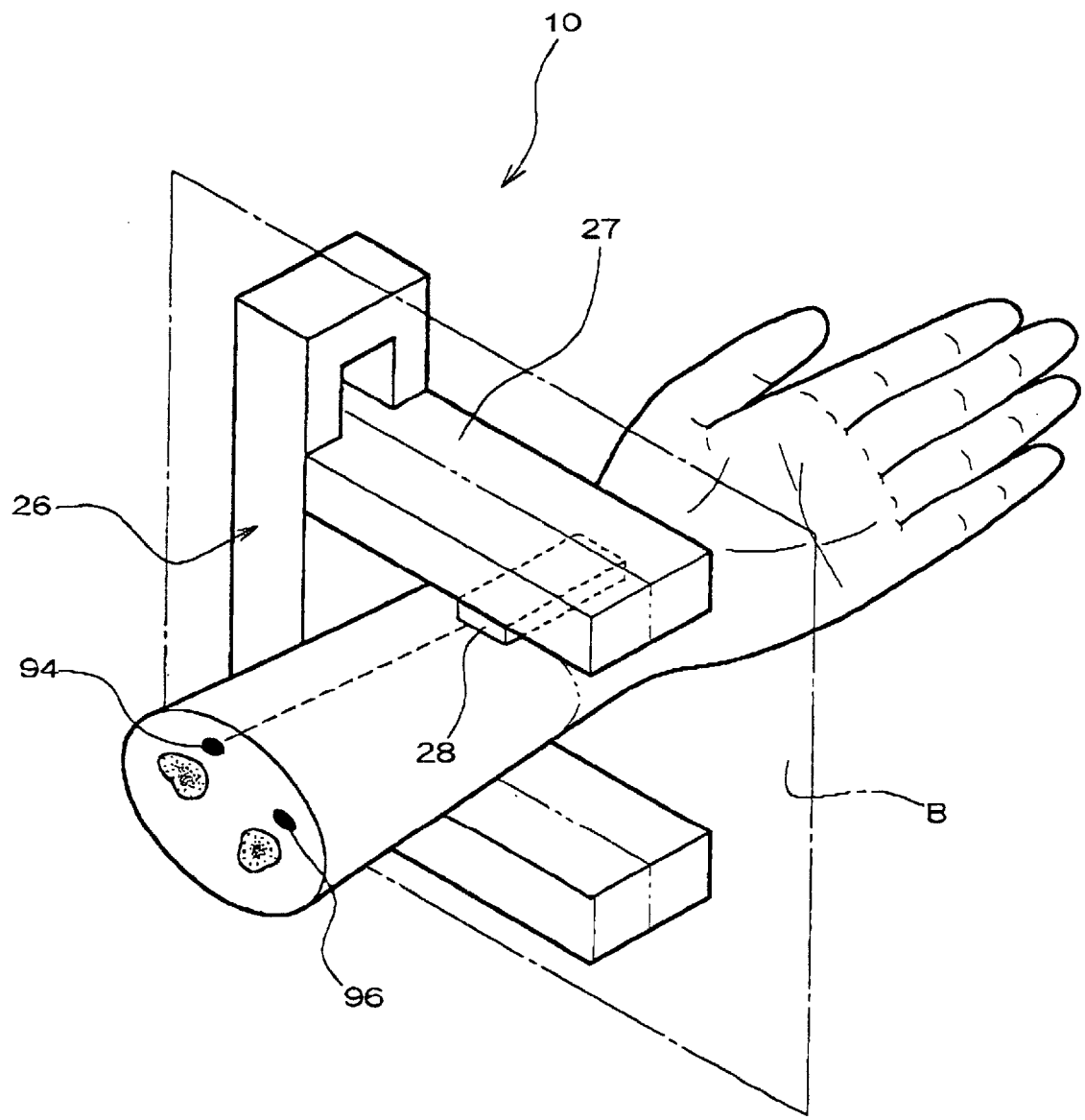
FIG. 1 is an oblique view showing blood pressure measurement using the blood pressure monitor of one embodiment of the present invention.

A preferred embodiment of the present invention is specifically described below referring to the drawings.

1. First Embodiment
1.1 Configuration of Blood Pressure Monitor

Figure 2:
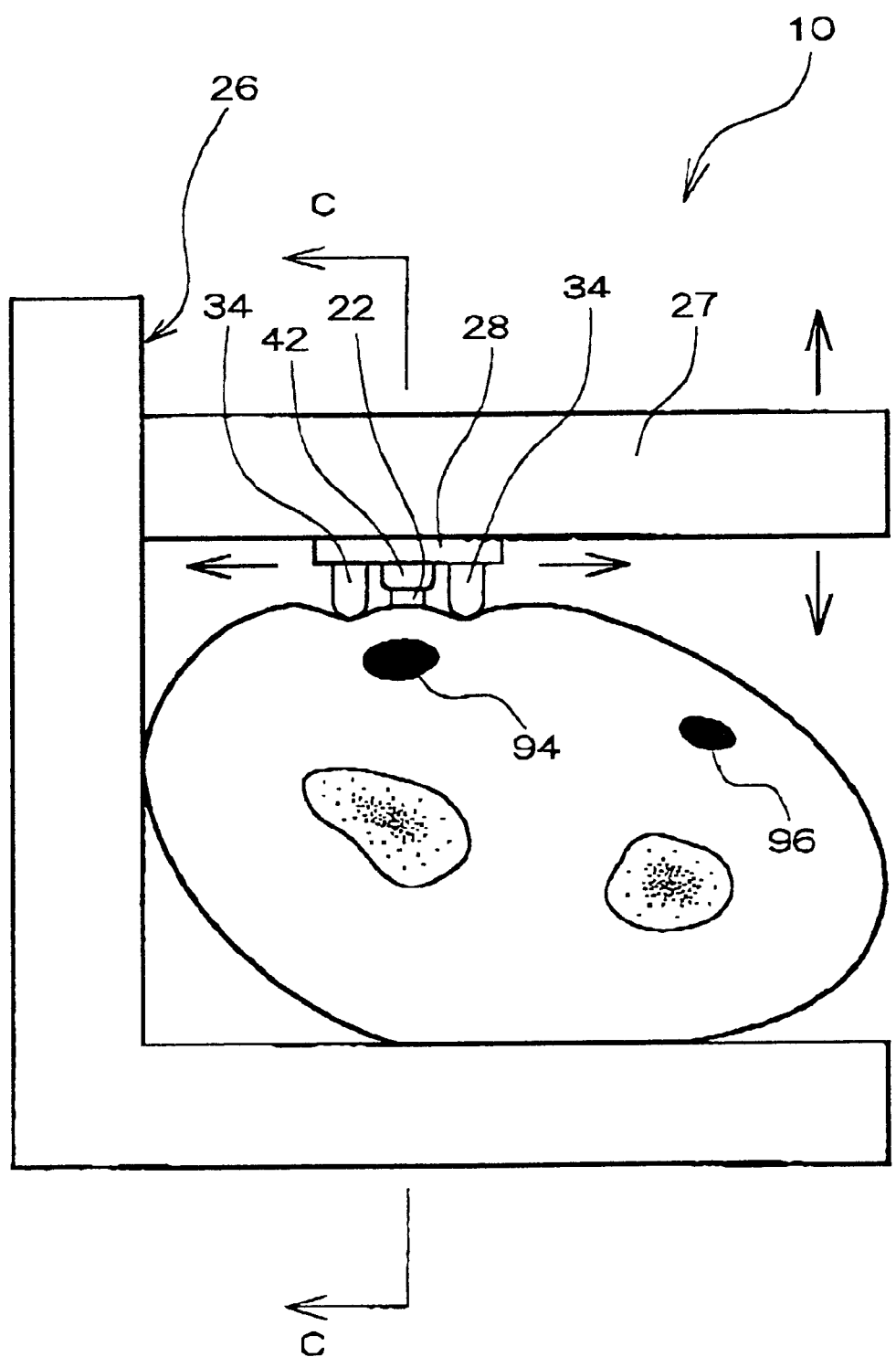
FIG. 2 is a cross-sectional view along the plane B in FIG. 1.
Figure 3:
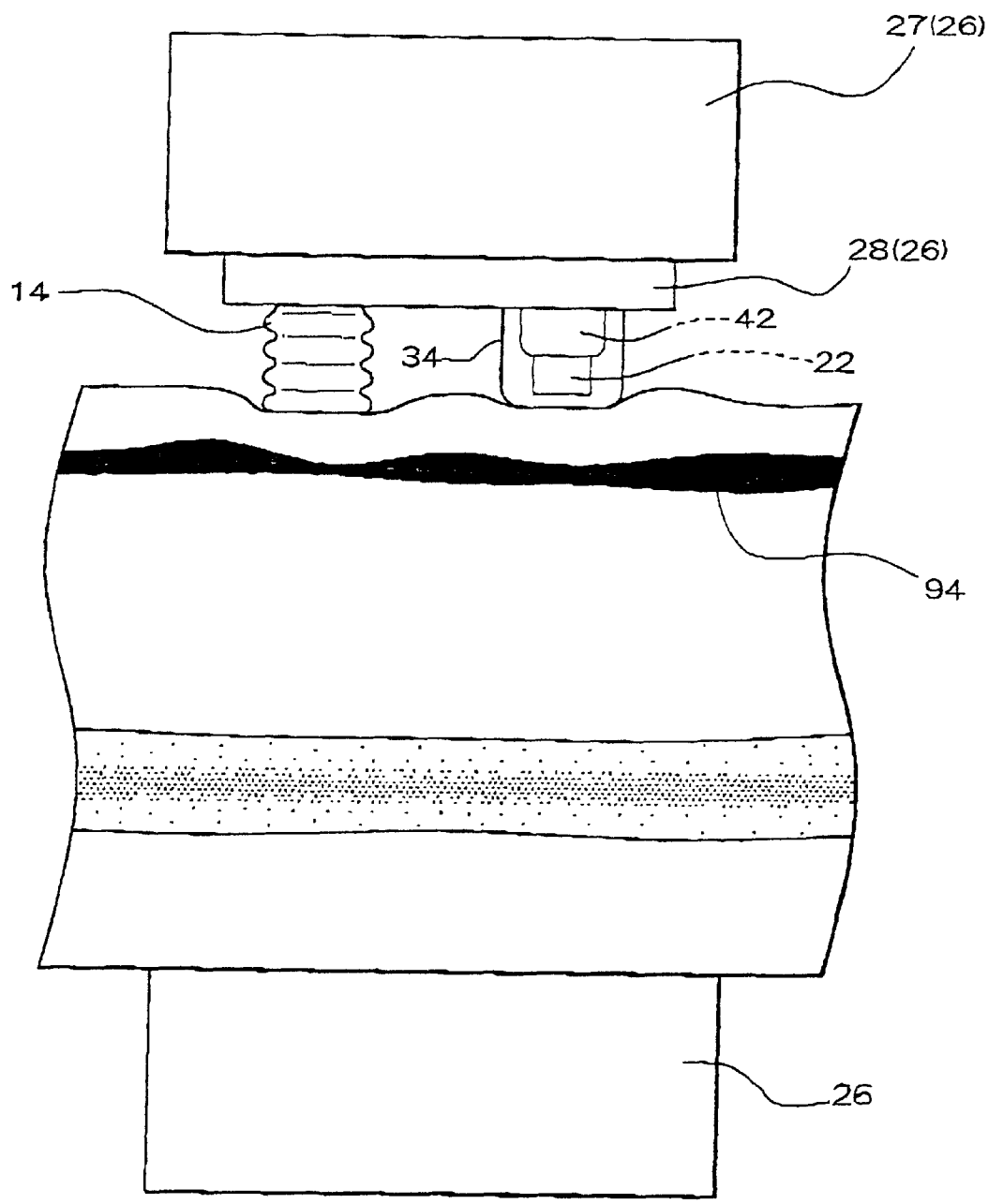
FIG. 3 is a longitudinal sectional view along the line C—C in FIG. 2.

FIG. 1 is an oblique view showing blood pressure measurement using the blood pressure monitor 10 of this embodiment. FIG. 2 is a cross-sectional view along the plane B in FIG. 1. FIG. 3 is a longitudinal sectional view along the line C—C in FIG. 2.

As shown in these figures, the blood pressure monitor 10 of this embodiment is equipped with a mounting mechanism 26 which determines positions for a vibration sensor 22, which detects pulses from the radial artery 94 in the wrist as sound or vibration, and the like, above the radial artery 94. The mounting mechanism 26 has a square configuration with one side open and has an upper side 27 capable of sliding up and down, driven by a driving mechanism not shown in the drawing. The upper side 27 has a slide block 28 on the back thereof which is secured movably along the longitudinal direction of the upper side 27, driven by a driving mechanism not shown in the drawing The mounting mechanism 26 is configured so as not to press all around the wrist, particularly not to come into contact with the ulnar artery 96 in which the many nerve tissues are present and which therefore tends to impart a disagreeable feeling if pressed.

As shown in FIG. 2 and FIG. 3, under the slide block 28 there are provided an artery pressing section 14, guides 34, and a vibration sensor 22 on the top of a sensor pressing section 42.

As shown in FIG. 3, the artery pressing section 14 locally presses the radial artery 94 from above the radial artery 94 on the proximal side from the vibration sensor 22. The pressure applied by the artery pressing section 14 is arbitrarily variable. The pressure applied by the artery pressing section 14 is a pressure securely set by feed-back using a pressure sensor which is incorporated as part of the artery pressing section. Blood flow to the peripheral side of the radial artery 94 can be interrupted or restricted by adjusting the pressure applied by the artery pressing section 14.

The vibration sensor 22 detects mechanical vibration or sound on the peripheral side or the artery pressing section 14 above the radial artery 94. For example, a pressure sensor, acceleration sensor, distortion sensor, or microphone can be used as the vibration sensor 22. It is sufficient for the vibration sensor 22 in this embodiment to detect the presence or absence of vibration due to pulse.

The sensor pressing section 42 is provided under the slide block 28 and causes the vibration sensor 22 secured on the sensor pressing section 42 to press the radial artery 94. This pressure can be adjusted by controlling the control section 18 so that the vibration sensor 22 can detect the vibration conveyed from the radial artery 94 in an optimum condition.

The guides 34 are provided, one on each side of the vibration sensor 22 as shown in FIG. 2. The vibration sensor 22 is guided along the radial artery 94 by locating the guides 34 on each side of the radial artery 94.

Figure 4:
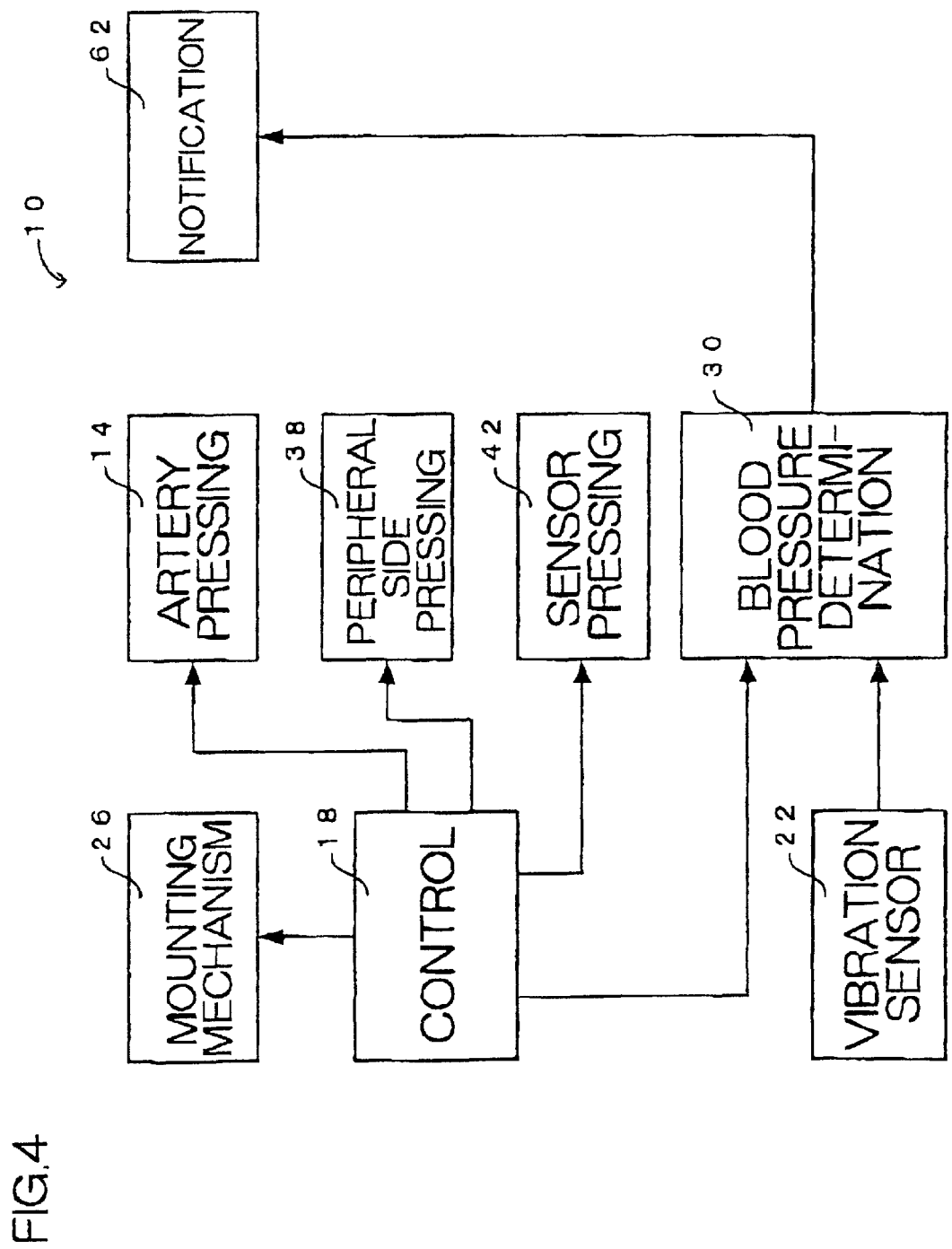
FIG. 4 is a block diagram showing the electric configuration of the blood pressure monitor of the first embodiment.

FIG. 4 is a block diagram showing the electric configuration of the blood pressure monitor 10 of this embodiment. As shown in this Fig., the blood pressure monitor 10 is provided with a control section 18, a blood pressure determination section 30, and a notification section 62 in addition to the previously described sections. These sections may be incorporated in a mounting mechanism 26, for instance, or may be independently formed and electrically connected with the mounting mechanism 26, vibration sensor 22, and pressing sections 14, 42, etc.

The control section 18 controls the pressure applied to the radial artery 94 by the artery pressing section 14 so that the artery pressing section 14 may press the radial artery 94 at various pressures in a prescribed range. The control section 18 also controls the pressure applied to the vibration sensor 22 by the sensor pressing section 42. The control section 18 further controls positioning by the mounting mechanism 26. The control section 18 comprises, for example, a CPU and a memory which stores a program for operating the CPU.

The blood pressure determination section 30 takes information on various pressures applied by the artery pressing section 14 from the control section 18, and determines the maximum and minimum blood pressures based on the information regarding the presence or absence of detected a vibration or the detected signals which are provided by the vibration sensor 22 at each of these various pressures. The blood pressure determination section 14 comprises, for example, a CPU and a memory which stores a program for operating the CPU.

The notification section 62 may comprise a display section which indicates the blood pressure values determined by the blood pressure determination section 30 as characters, a graph, or the like, such as an LCD, CRT, plotter, or printer, for example, or may comprise a sound creation section which indicates the blood pressure values by sound, such as a combination of a sound synthesizer and a speaker, for example.

1.2 Operation of Blood Pressure Monitor

The blood pressure monitor 10 operates as follows, for example, to measure blood pressure.

The section to be measured, for example, the wrist is placed in the prescribed position so that the radial artery 94 of the wrist may be located close to the vibration sensor 22 of the mounting mechanism 26 and the palmar side of the wrist may face the surface 27 of the mounting mechanism 26.

Next, the surface 27 of the mounting mechanism 26 is caused to descend so that the vibration sensor 22 comes into contact with the wrist.

Next, the slide block 28 is moved until the vibration sensor 22 and the artery pressing section 14 come above the radial artery 94. In this instance, these sections can be easily positioned by causing the guides 34 to be located on each side of the radial artery 94 by utilizing the engagement due to positioning of the radial artery 94 below these sections.

The pressure of the sensor pressing section 42 is adjusted by controlling the control section 18 so that the radial artery 94 is pressed in an optimum state for the vibration sensor 22 to detect the vibration from the radial artery 94.

Next, the pressure applied by the artery pressing section 14 located over the radial artery 94 is changed to various values by the control section 18 within the range slightly exceeding the commonly encountered blood pressure values, for example, in the range from 250 to 20 mmHg.

In each point pressed by the artery pressing section 14, the vibration sensor 22 located on the peripheral side of the artery pressing section 14 on the radial artery 94 detects a vibration of the blood flow which flows through blood vessels constricted by the artery pressing section 14. The detected signals are monitored. The result for each pressure by the artery pressing section 14 is stored in blood pressure determination section 30. Each pressing force value applied by the artery pressing section 14 is transmitted to the blood pressure determination section 30 from the control section 18 which controls the pressing force value.

The blood pressure determination section 30 determines the blood pressure when a sufficient number of pressure samples is obtained over the above-mentioned range for the artery pressing section 14. Specifically, the blood pressure determination section 30 determines the highest pressure of the artery pressing section 14 detected by the vibration sensor 22 which detects a vibration of the blood flowing through the constricted blood vessels as the maximum blood pressure, and the lowest pressure of the artery pressing section 14 detected by the vibration sensor 22 which detects a vibration of the blood flowing through the constricted blood vessels as the minimum blood pressure. The principle of blood pressure determination is the same as in the common auscultation method in which the blood pressure is determined by monitoring the vibration of the blood vessel when the blood flows through the vessel which is constricted by the pressure applied to the brachium on the peripheral side using a brachium band while changing the pressure in the brachium band.

Figure 5:
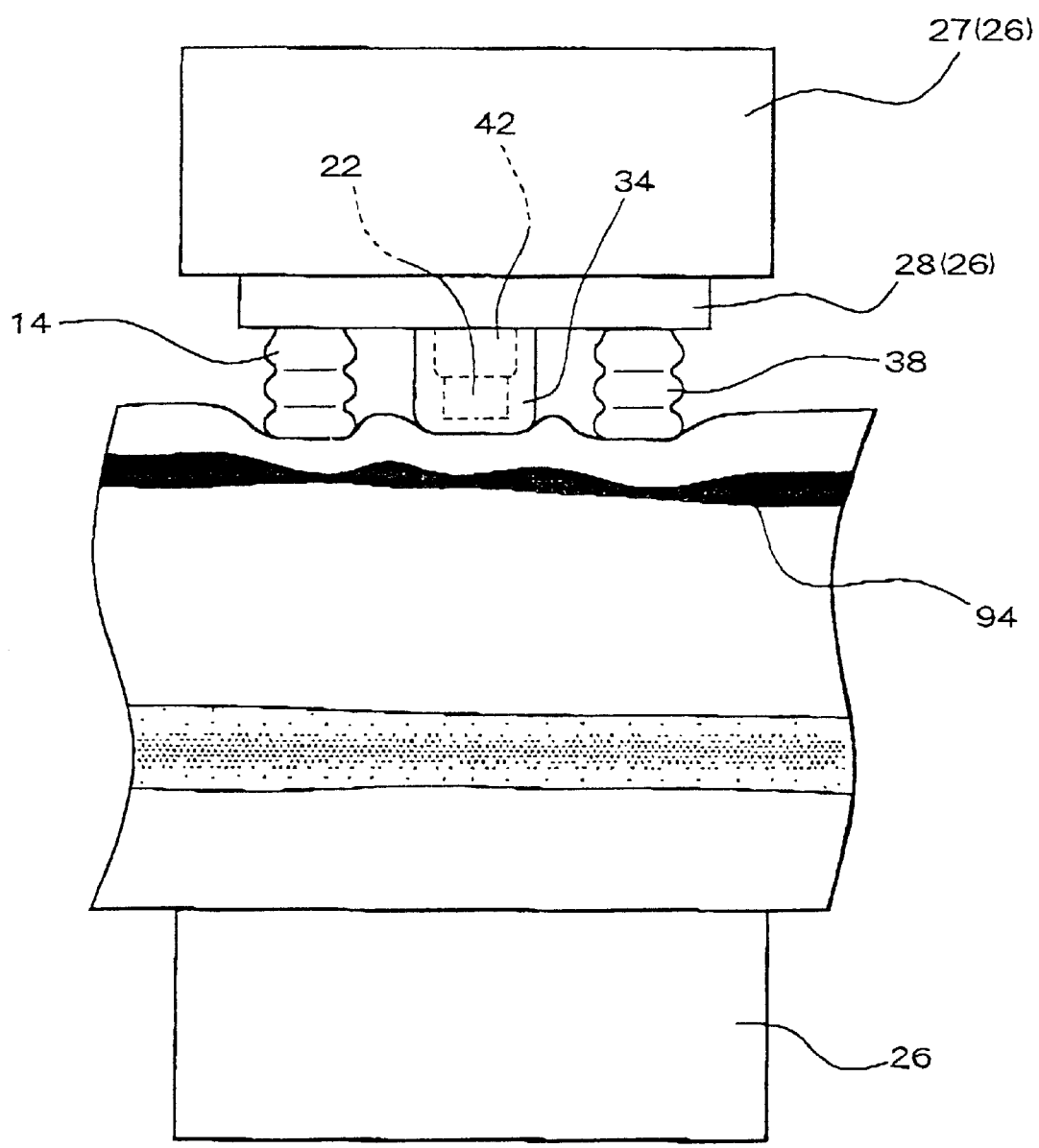
FIG. 5 is a longitudinal sectional view showing a modification of the first embodiment.

The information on the maximum and minimum blood pressures thus determined is transmitted to the notification section 62, and presented by the notification section 62 as a display such as a numerical value or a graph, printed characters, or as a voice 1.3 Modification of the First Embodiment 1.3.1 As shown in FIG. 5, which corresponds to the above-described FIG. 3 and shows a longitudinal sectional view of this modified embodiment, the blood pressure monitor 10 of this embodiment may have a peripheral side pressing section 38 provided above the radial artery 94 on the peripheral side from the vibration sensor 22, in addition to the artery pressing section 14 which is provided above the radial artery 94 on the proximal side from the vibration sensor 22. The peripheral side pressing section 38 presses the radial artery 94 prior to or simultaneously with the start of blood pressure measurement to shut off the pulse reversibly conveyed from the radial artery 94 on the peripheral side of the vibration sensor 22. Therefore, it is possible to shut off pulses conveyed from branches and the like of the artery, thus preventing such pulses from affecting the blood pressure measurement. As a result, accuracy of the blood pressure measurement can be improved.

Figure 6:
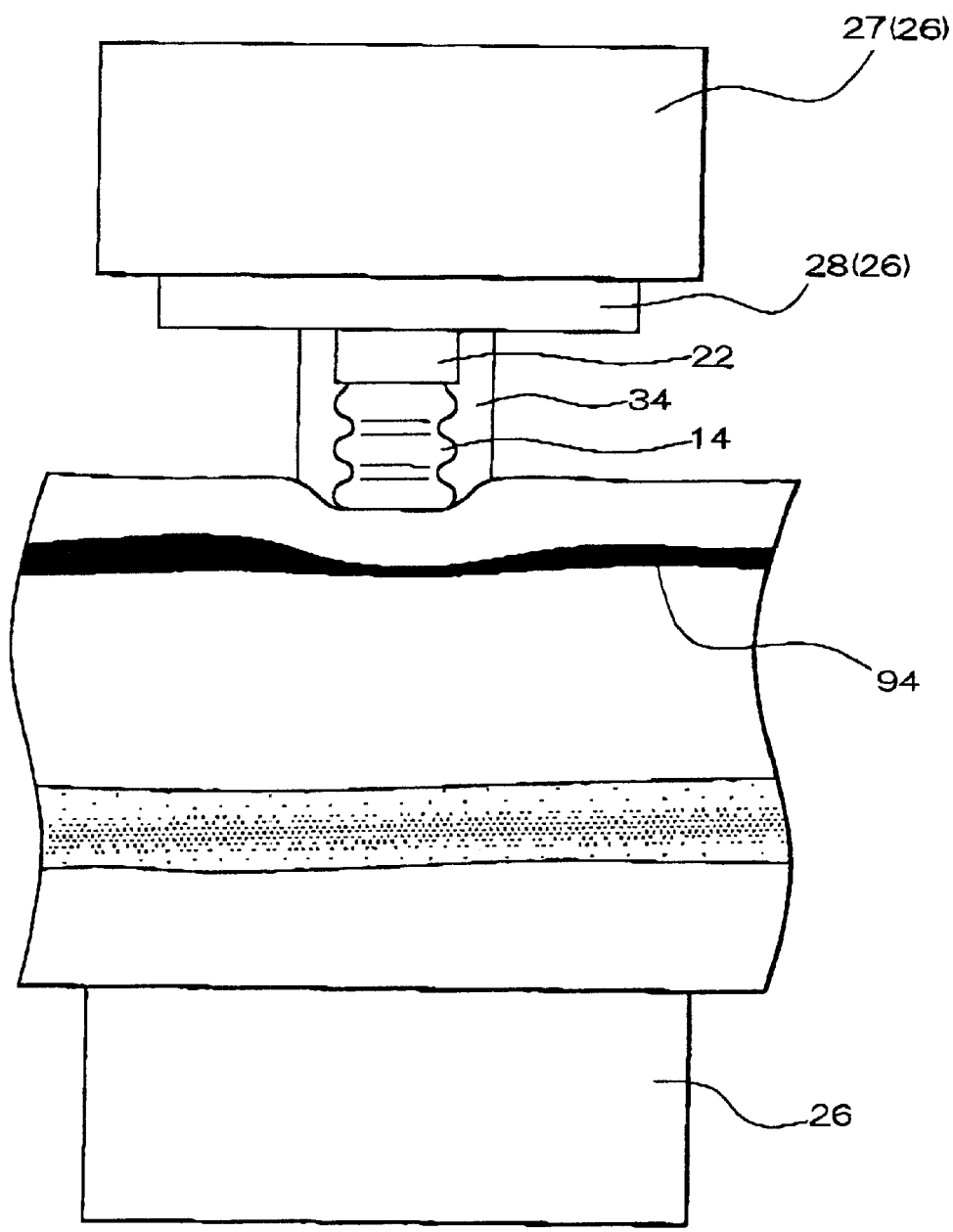
FIG. 6 is a longitudinal sectional view showing another modification of the first embodiment.

1.3.2 As shown in FIG. 6, which corresponds to the above-described FIG. 3 and shows a longitudinal sectional view of this modified embodiment, the blood pressure monitor 10 of this embodiment may have the artery pressing section 14 provided on the vibration sensor 22, which presses the radial artery 94 to enable the vibration sensor 22 to detect the vibration transmitted via the artery pressing section 14. In this case, it is unnecessary to provide the sensor pressing section 42 between the vibration sensor 22 and the slide block 28. In addition, the guides 34 have a height almost equivalent the total lengths of the vibration sensor 22 and the sensor pressing section 42, with one guide 34 being located on each side of the vibration sensor 22 and the artery pressing section 14. According to this modified embodiment, the blood pressure can be measured without causing the oscillatory sensor 22 to directly come into contact with the skin above the radial artery.

Figure 7:
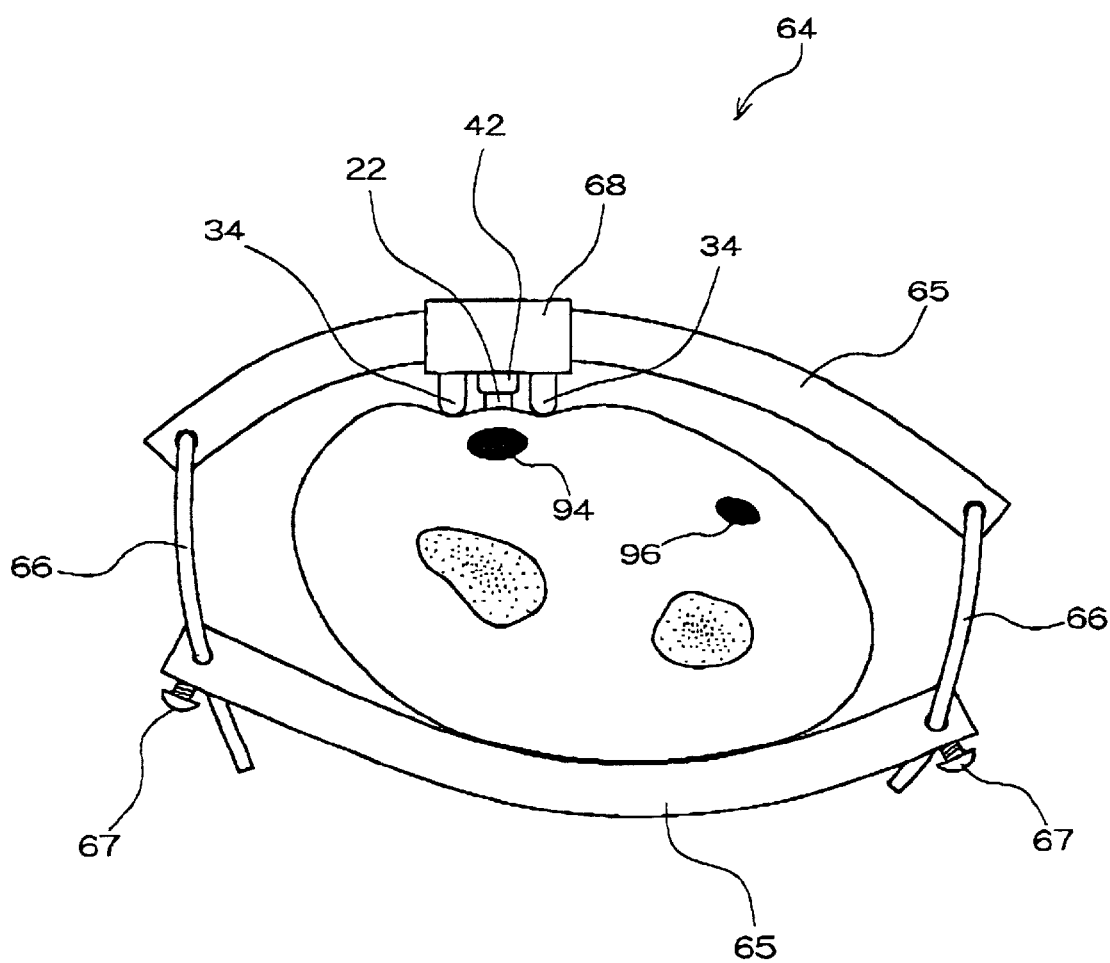
FIG. 7 is a longitudinal sectional view showing still another modification of the first embodiment.

1.3.3 The mounting mechanism as a positioning mechanism is not necessarily the one having the above-mentioned structure, but may be of the structure shown by the cross section view in FIG. 7, for example. This mounting mechanism 64 is provided with two frame members 65, two vinculum-shaped members 66 which connect the frame members 65 so that the distance between them may be freely adjusted, and a sliding block 68 provided on one of the frame members 65 slidably driven by a drive mechanism which is not shown in the figure The vinculum-shaped members 66 may be secured to the frame members 65 by screws 67 to provide an appropriate space between the frame members 65. The mounting mechanism 64 is configured so as not to press all around the wrist, particularly not to come into contact with the ulnar artery in which many nerve tissues are present and which therefore tends to impart a disagreeable feeling if pressed. In the same manner as in the previously described embodiment, a vibration sensor 22, an artery pressing section 14 (not shown), guides 34, a sensor pressing section 42, and the like are provided on the slide block 68. The mounting mechanism 64 of this structure allows continuous measurement of the blood pressure while the subject is moving because the mounting mechanism 64 is portable if attached to the wrist or the like.

Figure 8:
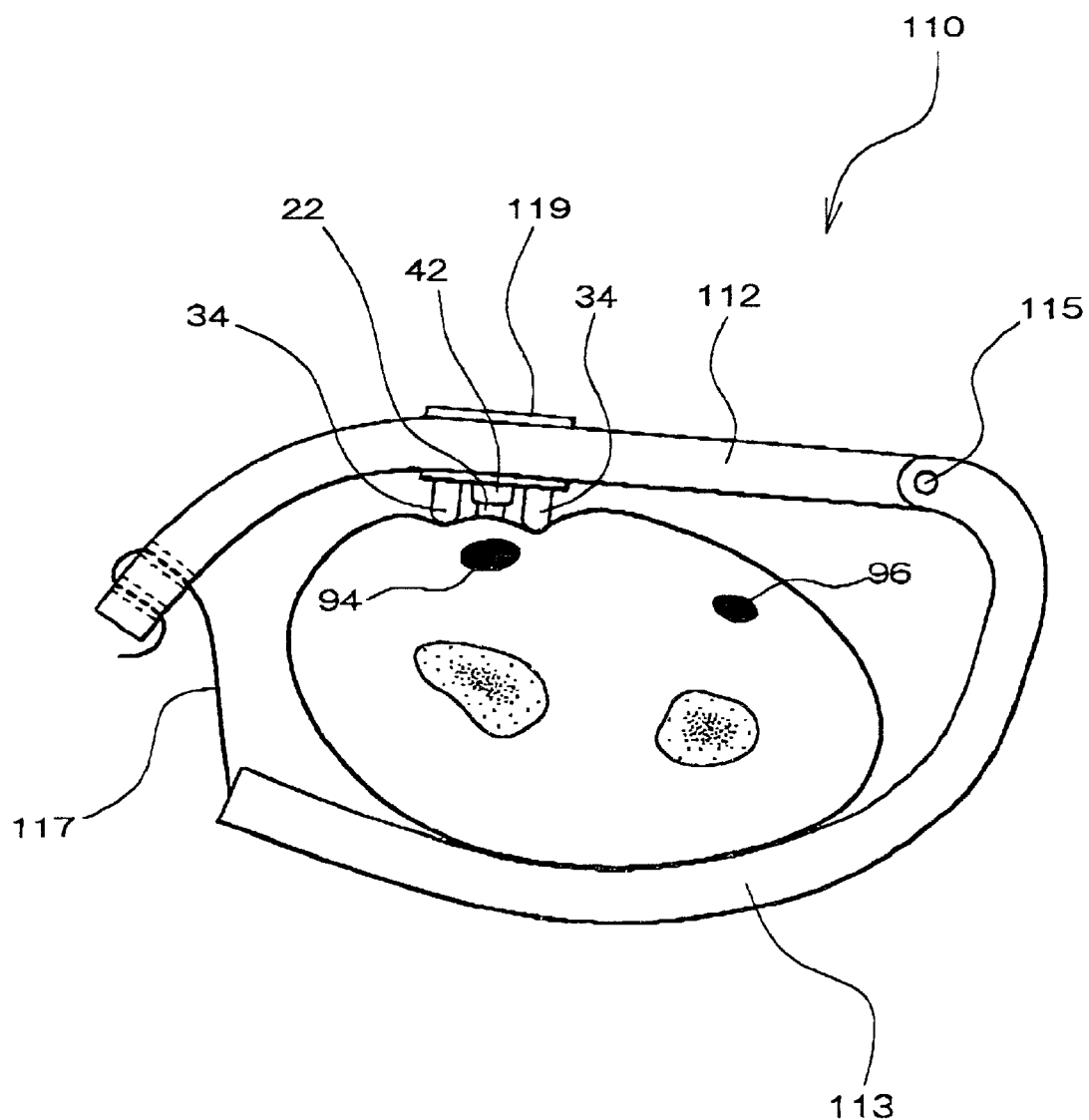
FIG. 8 is a longitudinal sectional view showing still another modification of the first embodiment.
Figure 9:
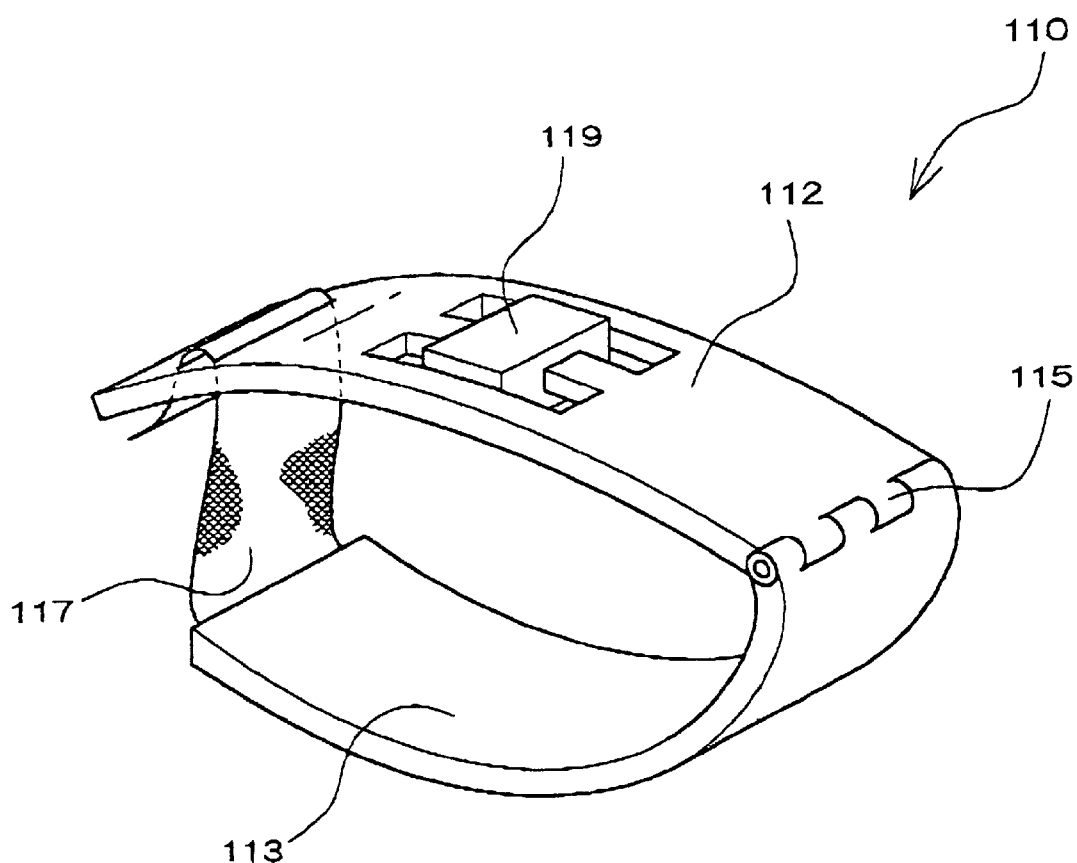
FIG. 9 is a perspective view of the modification shown in FIG. 8.

1.3.4 A mounting mechanism as a positioning mechanism may be configured as shown in a cross section view in FIG. 8 and a perspective view in FIG. 9. This mounting mechanism 110 is provided with two frame members 112 and 113 which are flexurally connected at a joining section 115, a cloth member 117 which adjusts the flexural conditions and connects the frame members 112 and 113 so as to maintain the adjusted flexural conditions, and a slide block 119 provided on one of the frame members 112 slidably driven by a drive mechanism which is not shown in the figure. As shown in FIG. 8, the mounting mechanism 110 is configured so as not to press all around the wrist, particularly not to come into contact with the ulnar artery in which many nerve tissues are present and which therefore tends to impart a disagreeable feeling if pressed. In the same manner as in the previously described embodiments, a vibration sensor 22, an artery pressing section 14 (not shown), guides 34, a sensor pressing section 42, and the like are provided on the slide block 119. The mounting mechanism 110 of this structure also allows continuous measurement of blood pressure while the subject is moving because the mounting mechanism is portable if attached to the wrist or the like.

Figure 10:
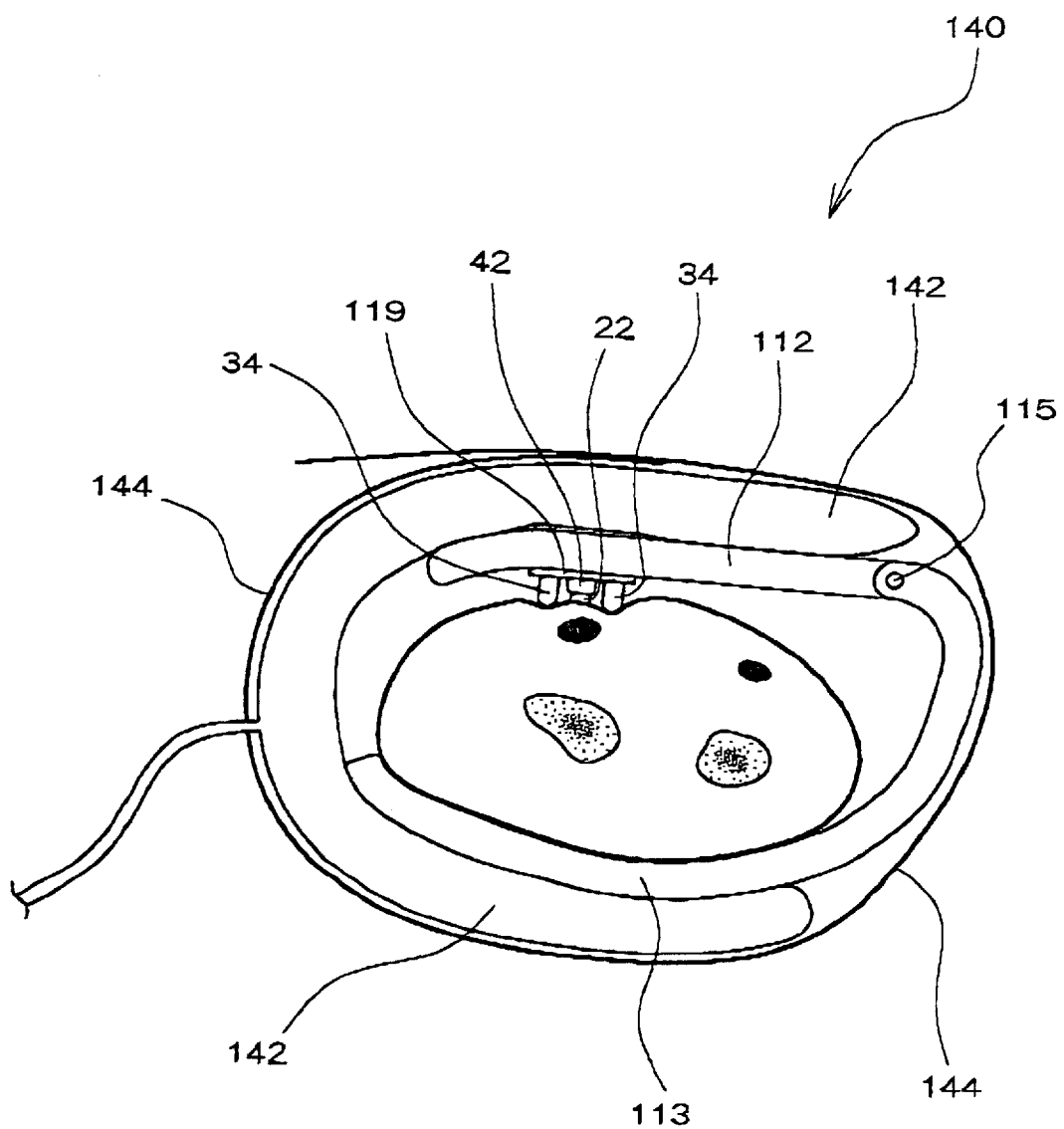
FIG. 10 is a longitudinal sectional view showing still another modification of the first embodiment.

1.3.5 Furthermore, a mounting mechanism as a positioning mechanism may be configured as shown in a cross section view in FIG. 10. This mounting mechanism 140 is almost the same as those shown in FIGS. 8 and 9, except that this mounting mechanism has no cloth member 117 which connects the frame members 112 and 113. In addition, this mounting mechanism 140 has an air bag 142, expandable by a gas such as air, provided around the frame members 112 and 113, and a band 144 which encloses the air bag 142. If air is filled in the air bag 142 enclosed by the band 144, the air bag provides pressure to the frame members 112 and 113 which causes these members to bend. This mounting mechanism 140 also has a slide block 119 provided on the frame member 112 slidably driven by a drive mechanism which is not shown in the figure. The mounting mechanism 140 is configured so as not to press all around the wrist, particularly not to come into contact with the ulnar artery 96 in which many nerve tissues are present and which therefore tends to impart a disagreeable feeling if pressed. In the same manner as in the previously described embodiments, a vibration sensor 22, an artery pressing section 14 (not shown), guides 34, a sensor press section 42, and the like are provided on the slide block 119. The mounting mechanism 140 of this structure also allows continuous measurement of blood pressure while the subject is moving because the mounting mechanism is portable if attached to the wrist or the like.

Figure 11:
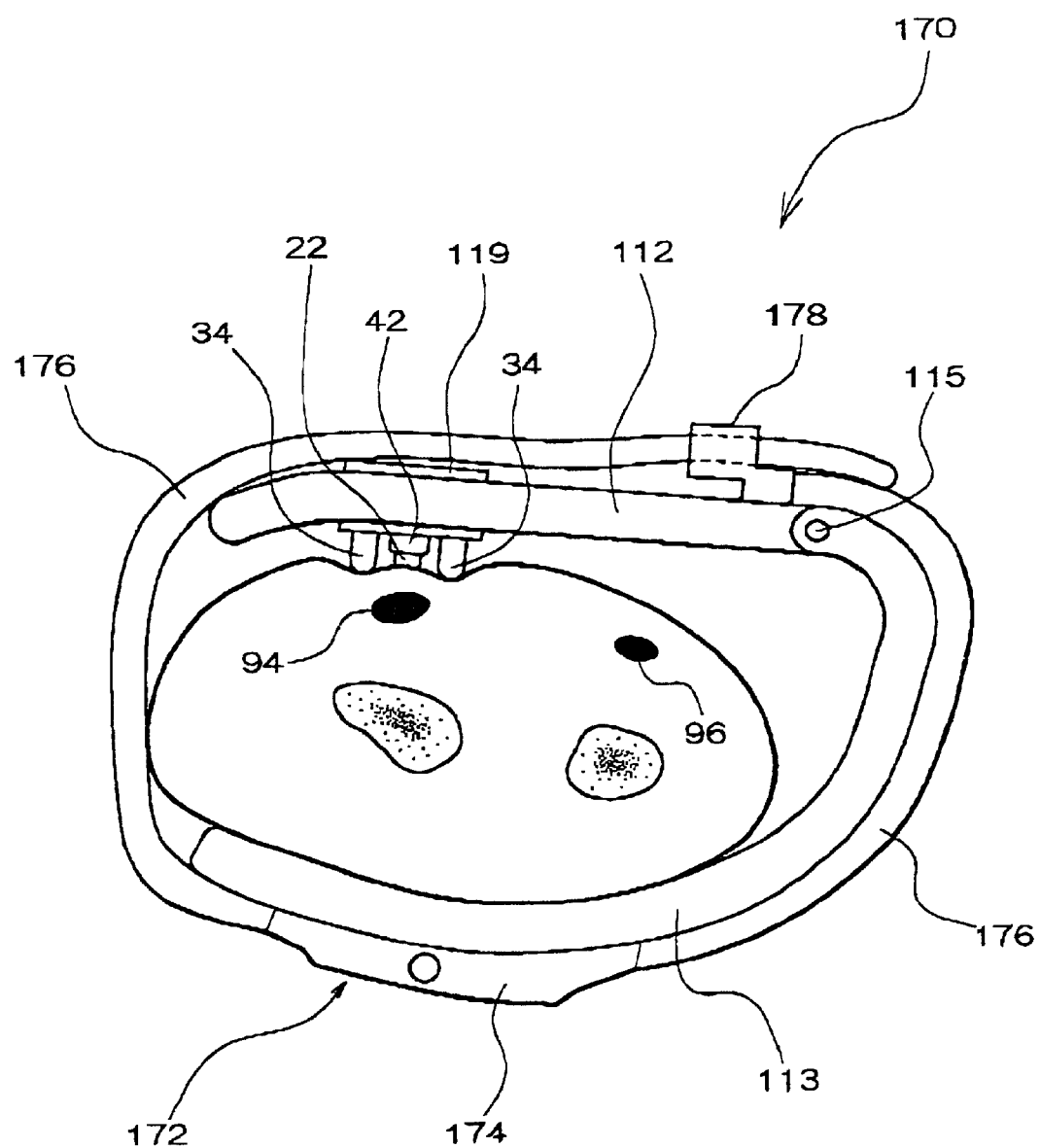
FIG. 11 is a longitudinal sectional view showing still another modification of the first embodiment.

1.3.6 Moreover, a mounting mechanism as a positioning mechanism may be configured as shown in a cross section view in FIG. 11. This mounting mechanism 170 is almost the same as those shown in FIGS. 8 and 9, except that this mounting mechanism has no cloth member 117 which connects the frame members 112 and 113 The mounting mechanism 170 is further provided with a clock-shaped member 172 around the circumference of the frame members 112 and 113. The clock-shaped member 172 has a main body 174, a belt 176, and a clamp 178, with the main body 174 being secured to the frame member 113. If the clock-shaped member 172 is fastened by the belt 176 and the belt 176 is clamped by the clamp 178, the clock-shaped member 172 can apply pressure to the frame members 112 and 113 so as to bend these members. The main body section 174 may house the above-mentioned control section 18, blood pressure determination section 30, notification section 62, and the like. The electric wiring connecting the main body 174 and the vibration sensor 22, artery pressing section 14, sensor pressing section 42, and the like which are provided on the slide block 119 is omitted from FIG. 11. This mounting mechanism 170 also has a slide block 119 provided on one of the frame members 112 slidably driven by a drive mechanism which is not shown in the figure. As shown in FIG. 11, the mounting mechanism 170 is configured so as not to press all around the wrist, particularly not to come into contact with the ulnar artery in which many nerve tissues are present and which therefore tends to impart a disagreeable feeling if pressed. In the same manner as in the previously described embodiments, a vibration sensor 22, an artery pressing section 14 (not shown), guides 34, a sensor press section 42, and the like are provided on the slide block 119. The mounting mechanism 170 of this structure also allows continuous measurement of blood pressure while the subject is moving because the mounting mechanism 64 is portable if attached to the wrist or the like.

1.3.7 In the above-mentioned embodiments, the radial artery 94 was taken as an example of artery to be pressed by the artery pressing section 14 for detection of a vibration using the vibration sensor 22. However, the artery pressed by the artery pressing section 14 for detection of a vibration using the vibration sensor 22 is not limited to the radial artery, but may be any artery in the extremities and fingers such as the ulnar artery of the wrist, the palmar finger artery, the brachial artery, the popliteal artery, and the like.

1.4 Effects of the First Embodiment

As described above, in the blood pressure monitor 10 of the present embodiment, the blood pressure determination section 30 determines the maximum and minimum pressures based on various pressing force values applied when the artery pressing section 14 locally presses an artery of the extremities or fingers, based on the signals which the vibration sensor detects based on a vibration of the blood flowing through blood vessels constricted by the artery pressing section 14. Because the extremities or fingers are not pressed over the entire circumference by the artery pressing section 14, no discomfort or unfavorable feeling will be imparted to the subject.

In addition, because the blood pressure monitor 10 of this embodiment is provided with mounting mechanisms 26, 64, 110, 140, 170 as a positioning mechanism, the artery pressing section 14 and the vibration sensor 22 can be easily positioned on the artery. Moreover, because mounting mechanisms 26, 64, 110, 140, 170 are designed so as not to press over the entire circumference the extremities or fingers, no discomfort or unfavorable feeling will be imparted to the subject.

Because the blood pressure monitor 10 of this embodiment is provided with the guides 34 which guide the vibration sensor 22 on the artery on each side of the artery, it is possible to locate the vibration sensor on the artery easily and with certainty.

Because the blood pressure monitor 10 is designed so as to cause the sensor pressing section 42 of the vibration sensor 22 to press the artery, it is possible for the vibration sensor to press the artery at an appropriate pressure so that a vibration from the artery can be detected with certainty.

2. Second Embodiment

The second embodiment differs from the first embodiment in that this embodiment uses a pulse wave sensor instead of the vibration sensor, is provided with a conversion section for converting a pulse wave into a blood pressure waveform, and a blood-pressure-waveform processing section for introducing various indicators based on the blood pressure waveform, and has a notification section which can provide not only information on the maximum and minimum blood pressures, but also information on the blood pressure waveform converted by the conversion section and various indicators introduced by the blood-pressure-waveform processing section. Other features are the same as in the first embodiment, so description thereof is omitted corresponding sections in each figure are indicated by the same symbols as in the first embodiment.

2.1 Configuration of Blood Pressure Monitor

In the same manner as in the first embodiment, the blood pressure monitor of this embodiment is provided with a mounting mechanism 26 as a positioning mechanism, guides 34, an artery pressing section 14, a peripheral side pressing section 38, a sensor pressing section 42, a control section 18, a blood pressure determination section 30, and a notification section 62.

Figure 12:
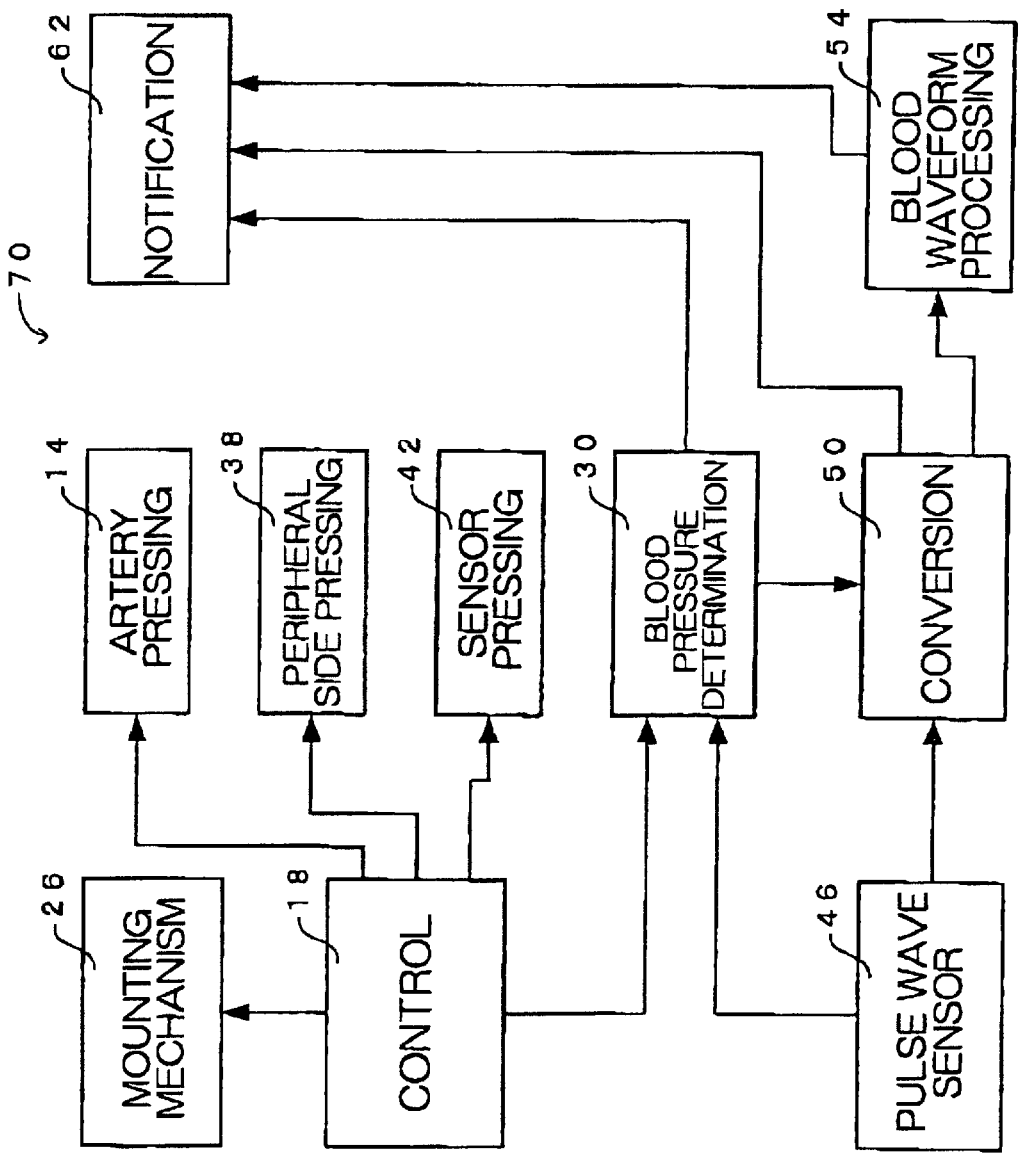
FIG. 12 is a block diagram showing the electric configuration of the blood pressure monitor of a second embodiment.

FIG. 12 is a block diagram showing the electric configuration of the blood pressure monitor 70 of this embodiment. As shown in this FIG., the blood pressure monitor 70 is provided with a pulse wave sensor 46 in place of the vibration sensor 22 of the first embodiment, and further provided with a conversion section 50 and a blood-pressure-waveform processing section 54.

The pulse wave sensor 46 detects not only the presence or absence of a pulse wave due to the flow of blood, but also pulse waveforms produced by pulse. A pressure sensor, acceleration sensor, distortion sensor, or microphone, for example, can be used as the pulse wave sensor 46.

The conversion section 50 converts pulse waveforms detected by the pulse wave sensor 46 into a blood pressure waveform using the information on the maximum and minimum blood pressures determined by the blood pressure determination section 30. The conversion section 50 comprises, for example, a CPU and a memory which stores a program for operating the CPU. In this manner, the blood pressure monitor obtains blood pressure waveforms by converting the pulse waveforms detected by the pulse wave sensor 46 located on the artery into blood pressure waveforms based on the maximum and minimum blood pressure measured by the blood pressure monitor. Thus, the instrument can non-invasively obtain blood pressure waveforms.

Figure 13:
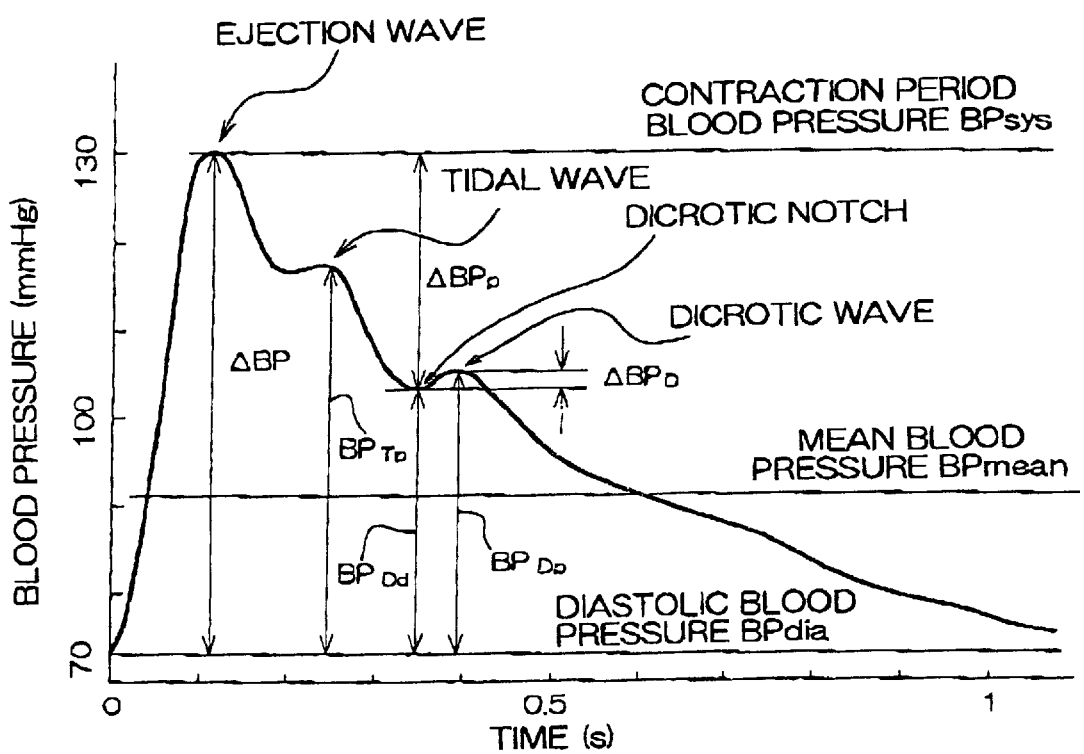
FIG. 13 is a graph showing a typical blood pressure waveform.

FIG. 13 is a graph showing a typical blood pressure waveform obtained in this manner. As shown in this figure, a blood pressure waveform of the artery typically has an ejection wave having a highest peak, a tidal wave having a second highest peak, a dicrotic wave having a third highest peak, and a dicrotic notch which is a valley between the tidal wave and dicrotic wave. The peak of the ejection wave corresponds to the contraction period blood pressure (maximum blood pressure) $BP_{eye}$. Diastolic blood pressure (minimum blood pressure) $BP_{dia}$ corresponds to the lowest blood pressure in the blood pressure waveform. The difference between the contraction period blood pressure $BP_{eye}$ and the diastolic blood pressure $BP_{dia}$ is called pulse pressure $\Delta BP$. The mean blood pressure $BP_{mean}$ is a temporal average of the blood pressure.

Based on the blood pressure waveform obtained by the conversion section 50, the blood-pressure-waveform processing section 54 calculates at least one of the following items; a mean blood pressure $BP_{mean}$, a pulse pressure $\Delta BP$ which is the difference between the maximum and minimum blood pressures, an after-ejection pressure $\Delta BP_P$ which is the difference between the dicrotic notch and the maximum blood pressure, a dicrotic wave height $\Delta BP_D$ which is the difference between the dicrotic notch and the dicrotic wave peak, an after-ejection pressure ratio $\Delta BP_P/\Delta BP$ which is the after-ejection pressure $\Delta BP_P$ normalized by the pulse pressure $\Delta BP$, and a dicrotic wave height after-ejection pressure ratio $\Delta BP_D/\Delta BP_P$ which is a ratio of the dicrotic wave height $\Delta BP_D$ and the after-ejection pressure $\Delta BP_P$.

The conversion section 50 and the blood-pressure-waveform processing section 54 may be incorporated in a mounting mechanism 26, for instance, or may be independently formed and electrically connected with the mounting mechanism 26, pulse wave sensor 46, and pressing sections 14, 42, etc.

The notification section 62 provides not only the information on the maximum blood pressure $BP_{eye}$ and the minimum blood pressure $BP_{dia}$, but also the information on blood pressure waveform converted by the conversion section 50 and various indicators made available by the blood-pressure-waveform processing section 54, such as a mean blood pressure $BP_{mean}$, pulse pressure $\Delta BP$, after-ejection pressure $\Delta BP_P$, dicrotic wave height $\Delta BP_D$, after-ejection pressure ratio $\Delta BP_P/\Delta BP$, and dicrotic wave height after-ejection pressure ratio $\Delta BP_D/\Delta BP_P$.

2.2 Operation of Blood Pressure Monitor

The operation of the blood pressure monitor 70 of this embodiment is the same as the operation of the blood pressure monitor 10 of the first embodiment up to the point where the blood pressure determination section determines the blood pressure. After determination of the blood pressure by the blood pressure determination section 30, the blood pressure monitor 70 which is provided with a pulse wave sensor 46 in place of the vibration sensor 22 is operated as follows.

The information on the maximum and minimum blood pressures determined by the blood pressure determination section 30 and the information on the pulse waveforms detected by the pulse wave sensor 46 are input into the conversion section 50.

Next, the conversion section 50 converts the pulse waveforms detected by the pulse wave sensor 46 using the information on the maximum and minimum blood pressures determined by the blood pressure determination section 30. (See FIG. 13)

Then, the information on the blood pressure waveform obtained by the conversion section 50 is input into the blood-pressure-waveform processing section 54. Based on the blood pressure waveform obtained by the conversion section 50, the blood-pressure-waveform processing section 54 calculates at least any one of the following items: a mean blood pressure $BP_{mean}$, a pulse pressure $\Delta BP$ which is the difference between the maximum blood pressure $BP_{eye}$ and the minimum blood pressure $BP_{dia}$, an after-ejection pressure $\Delta BP_P$ which is the pressure difference between the dicrotic notch and the maximum blood pressure, a dicrotic wave height $\Delta BP_D$ which is the pressure difference between the dicrotic notch and the dicrotic wave peak, an after-ejection pressure ratio $\Delta BP_P/\Delta BP$ which is the after-ejection pressure $\Delta BP_P$ normalized by the pulse pressure $\Delta BP$, and a dicrotic wave height after-ejection pressure ratio $\Delta BP_D/\Delta BP_P$ which is a ratio of the dicrotic wave height $\Delta BP_D$ and the after-ejection pressure $\Delta BP_P$.

The information on the blood pressure determined by the blood pressure determination section 30, information on the blood pressure waveform converted by the conversion section 50, information on various indicators made available by the blood-pressure-waveform processing section 54, and the like are input to the notification section 62. The notification section 62 presents the information as a display such as a numerical value or a graph, printed characters, or as a voice.

2.3 Modification of the Second Embodiment

The modification described for the first embodiment can be applied also to the second embodiment.

2.4 Effects of the Second Embodiment

As mentioned above, in the blood pressure monitor 70 of this embodiment the conversion section converts the pulse waveforms obtained from the pulse wave sensor 46 located on the artery into blood pressure waveforms based on the maximum and minimum blood pressures which are non-invasively measured by the blood pressure monitor 70. Therefore, blood pressure waveforms can be obtained non-invasively In addition, the blood pressure monitor 70 of this embodiment can cause the blood-pressure-waveform processing section 54 to make available at least one of the following items: a mean blood pressure $BP_{mean}$, a pulse pressure $\Delta BP$ which is the difference between the maximum and minimum blood pressures, an after-ejection pressure $\Delta BP_P$ which is the pressure difference between the dicrotic notch and the maximum blood pressure, a dicrotic wave $\Delta BP_D$ which is the pressure difference between the dicrotic notch and the dicrotic wave peak, an after-ejection pressure ratio $\Delta BP_P/\Delta BP$ which is the after-ejection pressure $\Delta BP_P$ normalized by the pulse pressure $\Delta BP$, and a dicrotic wave height after-ejection pressure ratio $\Delta BP_D/\Delta BP_P$ which is a ratio of the dicrotic wave height $\Delta BP_D$ and the after-ejection pressure $\Delta BP_P$.

3. Third Embodiment

The third embodiment differs from the first embodiment in that the former blood pressure monitor is provided with a second artery pressing section. Other features are the same as in the first embodiment, so description thereof is omitted. Corresponding sections in each figure are indicated by the same symbols as in the first embodiment.

3.1 Configuration of Blood Pressure Monitor

In the same manner as in the blood pressure monitor 10 of the first embodiment, the blood pressure monitor 76 of this embodiment is provided with a mounting mechanisms 26 as a positioning mechanism, guides 34, an artery pressing section 14 as a first artery pressing section, a sensor pressing section 42, a control section 18, a blood pressure determination section 30, and a notification section 62.

Figure 14:
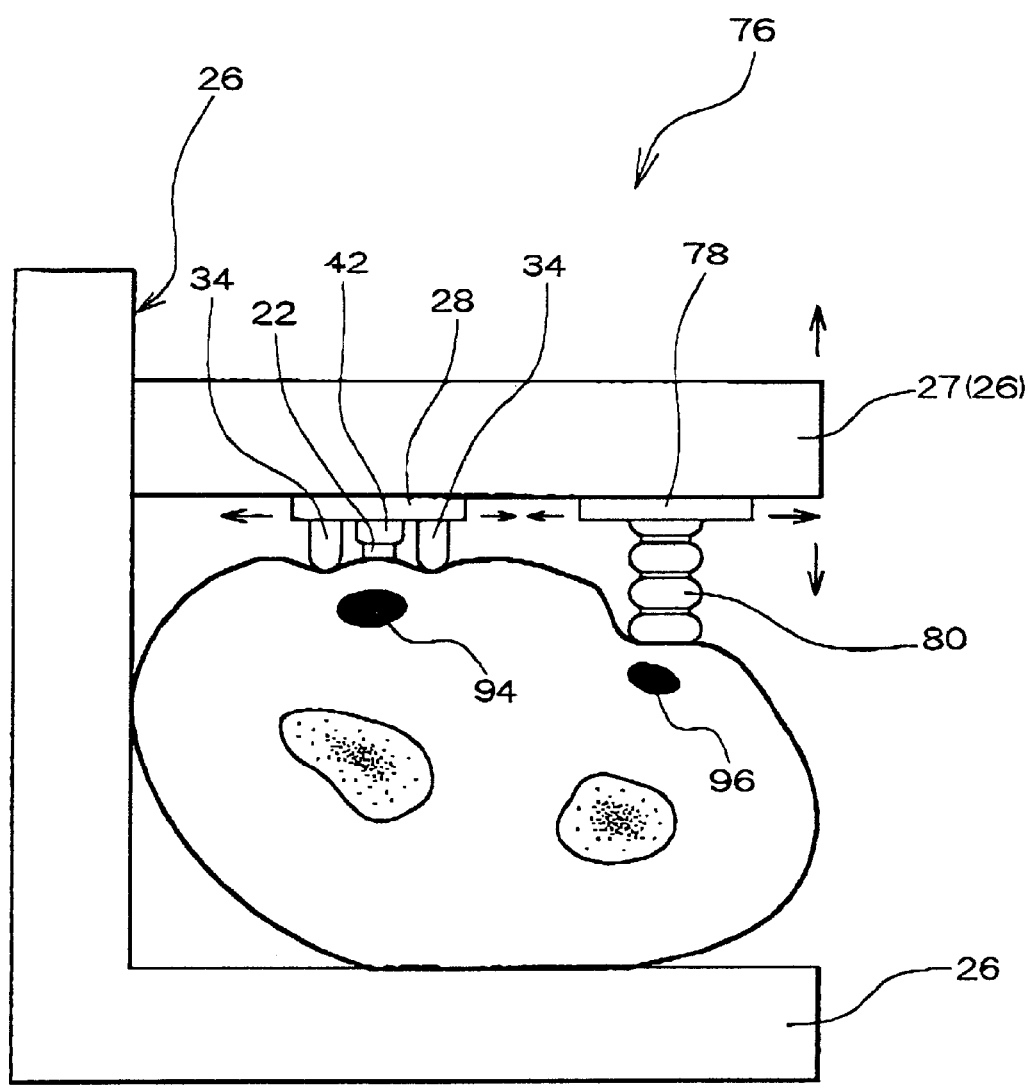
FIG. 14 is a cross-sectional view showing blood pressure measurement using the blood pressure monitor of a third embodiment of the present invention.
Figure 15:
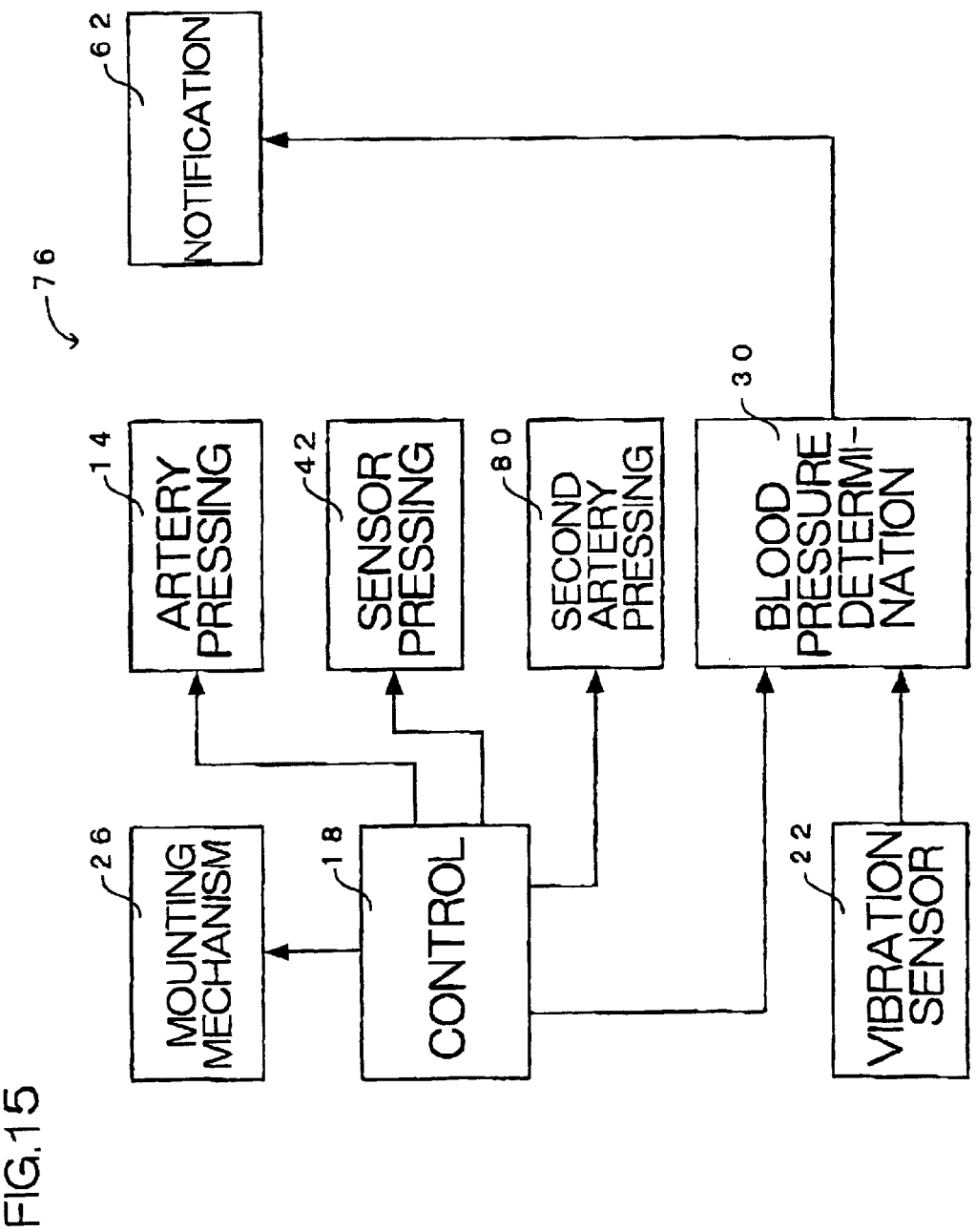
FIG. 15 is a block diagram showing the electric configuration of the blood pressure monitor of the third embodiment.

FIG. 14, which corresponds to FIG. 2 for the first embodiment, is a cross section view showing blood pressure measurement using the blood pressure monitor 76 of this embodiment. FIG. 15 is a block diagram showing the electric configuration of the blood pressure monitor 76 of this embodiment. As shown in this figure, the blood pressure monitor 76 of this embodiment is provided with a second artery pressing section 80 which presses the ulnar artery 96 as a second artery.

The second artery pressing section 80 is formed on the 2S second slide block 78 which can slide along the back of the surface 27 of the mounting mechanism 26. when measuring the blood pressure, the second artery pressing section 80 presses the ulnar artery 96, which is the second artery in the wrist, with the controlling action of the control section 18, thereby interrupting with blood flow to the peripheral side.

3.2 Operation of Blood Pressure Monitor

Operation of the blood pressure monitor 76 of this embodiment differs from that of the first embodiment in that the former requires additional procedure for operating the second artery pressing section 80 which presses the ulnar artery 96 when measuring the blood pressure.

Specifically, a slide block 78 on which the second artery pressing section 80 is provided is moved so as to position the second artery pressing section 80 on the ulnar artery upper 94 in almost the same timing as in the operation described in connection with the first embodiment, in which the slide block 28, on which the vibration sensor 22, artery pressing section 14, and guides 34 are provided, is positioned on the radial artery 94. Then, the second artery pressing section 80 presses the ulnar artery 96 with the controlling action of the control section 18, whereby blood flow to the peripheral side is interrupted. The blood pressure is measured at the time of, or after, the interruption of blood flow to the peripheral side by such pressure application to the ulnar artery 96 by the second artery pressing section 80.

Except for the above-mentioned operation, the operation of the blood pressure monitor 76 of this embodiment is the same as the operation of the blood pressure monitor 10 of the first embodiment.

3.3 Modification of the Third Embodiment

The modification described for the first embodiment can be applied also to the third embodiment. In addition, the following modification is possible in this embodiment.

Figure 16:
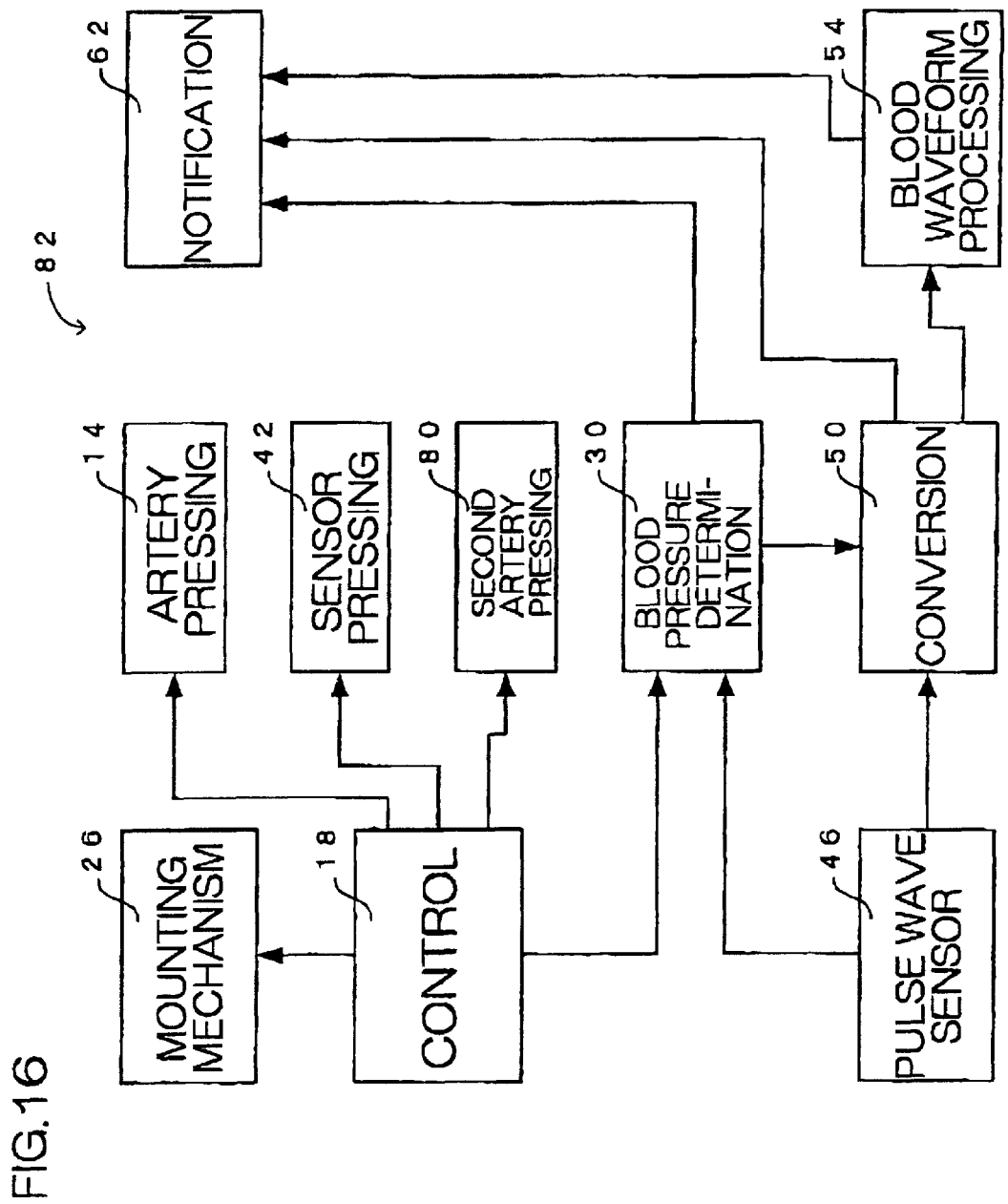
FIG. 16 is a block diagram showing a modification of the electric configuration of the blood pressure monitor of the third embodiment.

3.3.1 Similar to the differences between the first and second embodiments, the modified blood pressure monitor 82 which differs from the above-described embodiment in that this modified embodiment uses a pulse wave sensor 46 instead of the vibration sensor 22, is provided with a conversion section 50 for converting a pulse waveform into a blood pressure waveform and a blood-pressure-waveform processing section 54 for introducing various indicators mentioned in the second embodiment based on the blood pressure waveform, and has a notification section 62 which can provide not only the information on the maximum and minimum blood pressures, but also information on the blood pressure waveform converted by the conversion section 50 and various indicators introduced by the blood-pressure-waveform processing section 54. FIG. 16 is a block diagram showing the electric configuration of the blood pressure monitor 82. The operation of the blood pressure monitor 82 is the same as the operation of the blood pressure monitor 70 of the second embodiment, except for the addition of the operation for the above-mentioned second artery pressing section 80. Therefore, in the blood pressure monitor 82 the conversion section 50 converts the pulse waveforms obtained from the pulse wave sensor 46 located on the artery into blood pressure waveforms based on the maximum and minimum blood pressures which are non-invasively measured by the blood pressure monitor 82. Therefore, blood pressure waveforms can be obtained non-invasively by the blood pressure monitor 82.

3.3.2 Although the above embodiment describes an example of the wrist wherein the first artery is the radial artery 94 and the second artery is the ulnar artery 96, the first artery of which the vibration is detected by the vibration sensor may be the ulnar artery 94 and the second artery of which the blood flow is interrupted by pressing the second artery pressing section 80 may be the radial artery.

It is also possible to apply this embodiment to fingers, in which case the first artery may be one of the palmar digital artery and the second artery the other palmar digital artery, for example. In this instance, a vibration in one of the palmar digital artery is detected by the vibration sensor 22, while the blood flow is interrupted by pressing the other palmar digital artery using the second artery pressing section 80. In this case, the upper side of the mounting mechanism 26 should be configured as a circle so that the vibration sensor 22 and the second artery pressing section 80 may press the finger from opposite sides.

3.4 Effects of the Third Embodiment

As described above, because the blood pressure monitors 76,82 of this embodiment are provided with the second artery pressing section 80 which locally presses the ulnar artery 96, the effect of pulse produced by blood flow from the ulnar artery on detection by the vibration sensor 22 or pulse wave sensor 46 can be prevented. As a result, accuracy of the blood pressure measurement can be improved.

4. Fourth Embodiment

The pulse wave detection apparatus of the fourth embodiment differs from the first embodiment in that the former is equipped with a pulse wave sensor in place of a vibration sensor, has no blood pressure determination section, and has a waveform processor. Other features are the same as in the first embodiment, so description thereof is omitted. Corresponding sections in each figure are indicated by the same symbols as in the first embodiment.

4.1 Configuration of Pulse Wave Detection Apparatus

In the same manner as in the first embodiment, the pulse wave detection apparatus 84 of this embodiment is provided with a mounting mechanism 26 as a positioning mechanism, guides 34, an artery pressing section 14, a sensor pressing section 42, a control section 18, and a notification section 62. The external appearance may be the same as the first embodiment.

Figure 17:
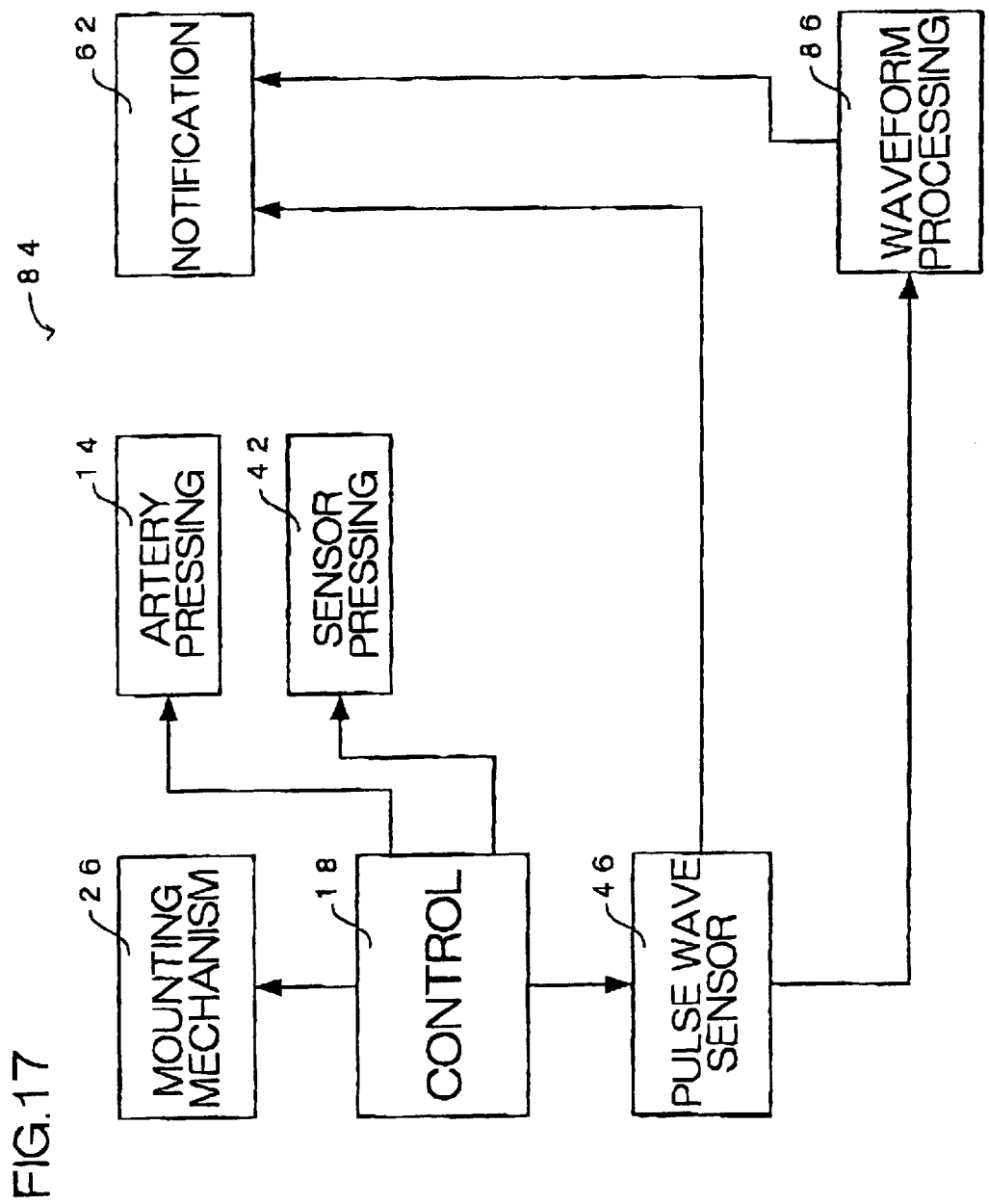
FIG. 17 is a block diagram showing the electric configuration of the pulse wave detection apparatus of a fourth embodiment.

FIG. 17 is a block diagram showing the electric configuration of the pulse wave detection apparatus 84 of this embodiment. As shown in this figure, the electric configuration of the pulse wave detection apparatus 84 of this embodiment differs from that of the blood pressure monitor 10 of the first embodiment shown in FIG. 4 in that the former is provided with a pulse wave sensor 46 in place of the vibration sensor 22, has no blood pressure determination section 30, and has a waveform processor 86.

The pulse wave sensor 46 detects not only the presence or absence of a pulse wave due to the flow of blood, but also pulse waveforms produced by pulse. A pressure sensor, acceleration sensor, distortion sensor, or microphone, for example, can be used as the pulse wave sensor 46.

Based on the pulse waveform detected by the pulse wave detection apparatus 46, the waveform processor 86 calculates the indicators showing pulse waveform characteristics, such as an after-ejection pressure ratio $\Delta BP_P/\Delta BP$ which is the ratio of the dicrotic wave height $\Delta BP_D$ (the pressure difference between the dicrotic notch blood pressure and the maximum blood pressure) and the pulse pressure $\Delta BP$ (the difference between the maximum and minimum blood pressures), a dicrotic notch difference ratio $BP_{Dd}/\Delta BP$ which is the ratio of the dicrotic notch difference $BP_{Dd}$ (the difference between the dicrotic notch pressure and the minimum blood pressure) and the pulse pressure $\Delta BP$ (the difference between the maximum and minimum blood pressures), a mean blood pressure pulse pressure ratio $BP_{mean}/\Delta BP$ which is the ratio of the mean blood pressure $BP_{mean}$ and the pulse pressure $\Delta BP$ (the difference between the maximum and minimum blood pressures), a dicrotic wave height ratio $\Delta BP_D/\Delta BP$ which is the dicrotic wave height $\Delta BP_D$ normalized by the pulse pressure $\Delta BP$, and a dicrotic wave height after-ejection pressure ratio $\Delta BP_D/\Delta BP_P$ which is the ratio of the dicrotic wave height $\Delta BP_D$ and the after-ejection pressure $\Delta BP_P$. (See FIG. 13)

The notification section 62 provides information on pulse waveforms detected by the pulse wave sensor 46 or various indices made available by the waveform processor 86, such as an after-ejection pressure ratio $\Delta BP_P/\Delta BP$, a dicrotic notch difference ratio $BP_{Dd}/\Delta BP$, a mean blood pressure pulse pressure ratio $BP_{mean}/\Delta BP$, a dicrotic wave height ratio $\Delta BP_D/\Delta BP$, and a dicrotic wave height after-ejection pressure ratio $\Delta BP_D/\Delta BP_{PP}$, for example.

4.2 operation of Pulse Wave Detection Apparatus

The pulse wave detection apparatus 84 operates as follows, for example, to detect pulses.

The section to be measured, for example, the wrist is placed in the prescribed position so that the radial artery 94 of the wrist may be located close to the pulse sensor 46 of the mounting mechanism and the palmar side of the wrist may face the surface 27 of the mounting mechanism 26.

Next, the surface 27 of the mounting mechanism 26 is caused to descend so that the pulse sensor 46 comes into contact with the wrist.

Next, the slide block 28 is moved until the pulse sensor 46 and the artery pressing section 14 come above the radial artery 94. In this instance, these sections can be easily positioned by causing the guides 34 to be located on each side of the radial artery 94.

The pressure of the sensor pressing section 42 is adjusted by controlling the control section 18 so that the radial artery 94 is pressed in an optimum state for the pulse sensor 46 to detect the pulse from the radial artery 94.

Next, the pressure applied by the artery pressing section 14 located on the radial artery 94 is changed to various values by the control section 18 within the range slightly exceeding the commonly encountered blood pressure values, for example, in the range from 200 to 30 mmHg, whereupon a pressure enabling the pulse wave sensor 46 to detect an optimum waveform pattern is selected.

The detected information on pulse waveforms is input into the waveform processor 86, where the information is processed into various indices characteristic to pulse waveform patterns, such as pulses, an after-ejection pressure ratio $\Delta BP_P/\Delta BP$, a dicrotic notch difference ratio $BP_{Dd}/\Delta BP$, a mean blood pressure pulse pressure ratio $BP_{mean}/\Delta BP$, a dicrotic wave height ratio $\Delta BP_D/\Delta BP$, and a dicrotic wave height after-ejection pressure ratio $\Delta BP_D/\Delta BP_P$, for example.

The information on pulse waveforms detected by the pulse wave sensor 4 6 and information on various indices made available by the waveform processor 86 are input to the notification section 62. The notification section 62 presents the information such as a pulse waveform, pulse, dicrotic notch difference pressure ratio, and mean blood pressure pulse pressure ratio, as a display such as a numerical value or a graph, printed characters, or as a voice.

4.3 Modification of the Fourth Embodiment

The modification described for the first embodiment can be applied also to the fourth embodiment.

4.4 Effects of the Fourth Embodiment

In this pulse wave detection apparatus 84, the pulse wave sensor 46 detects pulse waves at the point of the artery pressing section 14 or on the peripheral side based on variable pressing force values applied when the artery pressing section 14 locally presses the artery of the extremities or fingers. Therefore, pulse waves at various pressures applied by the artery pressing section 14 can be detected.

In addition, because the pulse wave detection apparatus 84 of this embodiment is provided with a mounting mechanisms 26 as a positioning mechanism, the artery pressing section 14 and the pulse wave sensor 46 can be easily positioned on the artery.

Because the pulse wave detection apparatus 84 of this embodiment is provided with guides which guide the pulse wave sensor on the artery on each side of the artery, it is possible to locate the pulse wave sensor 46 on the artery easily and with certainty.

Because the pulse wave detection apparatus 84 is designed so as to cause the sensor pressing section 42 of the pulse wave sensor 46 to press the artery, it is possible for the pulse wave sensor to press the artery at an appropriate pressure so that pulse wave from the artery can be detected with certainty.

5. Fifth Embodiment 5.1 Configuration of Blood Pressure Monitor

Figure 18:
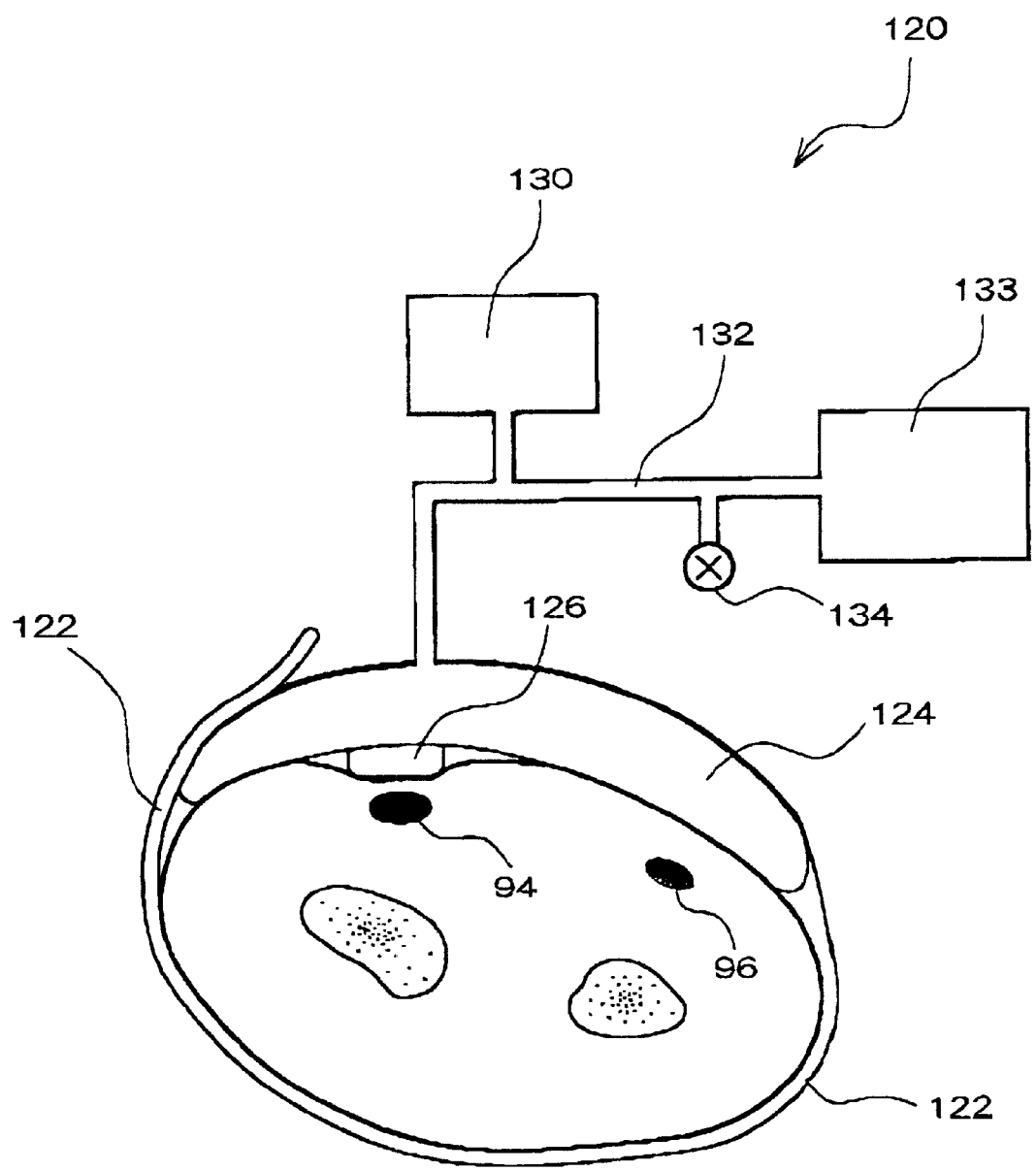
FIG. 18 is a schematic view showing blood pressure measurement using the blood pressure monitor of a fifth embodiment worn on the wrist.

FIG. 18 is a schematic view showing blood pressure measurement using the blood pressure monitor 120 of this embodiment worn on the wrist. As shown in this figure, the blood pressure monitor 120 of this embodiment is designed so that the blood pressure can be measured with a cuff-like band 122 wound around the wrist. The band 122 is provided with a pressure applying section 124 in the shape of a bag and an artery pressing section 126 protruding from the pressure applying section 124 in the inner side thereof, and is wound around the wrist so that the artery pressing section 126 may be located on the point corresponding to the radial artery 94. The artery pressing section 126 is designed so as to locally press the radial artery 94 to substantially shut off or restrict blood flow therein.

The pressure applying section 124 is formed in the shape of a bag to which a pump 133 and an exhaust valve 134 are connected via a tube 132. The volume of the pressure addition member 124 is controlled by adjusting the amount of the fluid, air, for example, filled in the pressure applying section 124 by using the pump 133 or the exhaust valve 134, whereby the pressure applied to the radial artery 94 by the artery pressing section 126 can be controlled. The pressure addition member 124 is of a sufficient size to be located on both the radial artery 94 and ulnar artery 96 at the same time.

The tube 132 is equipped with a pressure sensor 130 which detects the pressure change of the fluid. The pressure sensor 130 can detect a vibration of the radial artery 94, which is conveyed as a fluid pressure change via the artery pressing section 126 and the pressure applying section 124. specifically, because the artery pressing section 126 located above the radial artery 94 is dislocated corresponding to the vibration of the radial artery 94 and presses the pressure applying section 124 according to the dislocation, the fluid pressure in the pressure applying section 124 changes according to the vibration of the radial artery 94. Accordingly, the pressure sensor 130 which detects such a pressure change can output signals corresponding to the vibration of the radial artery 94.

Figure 19:
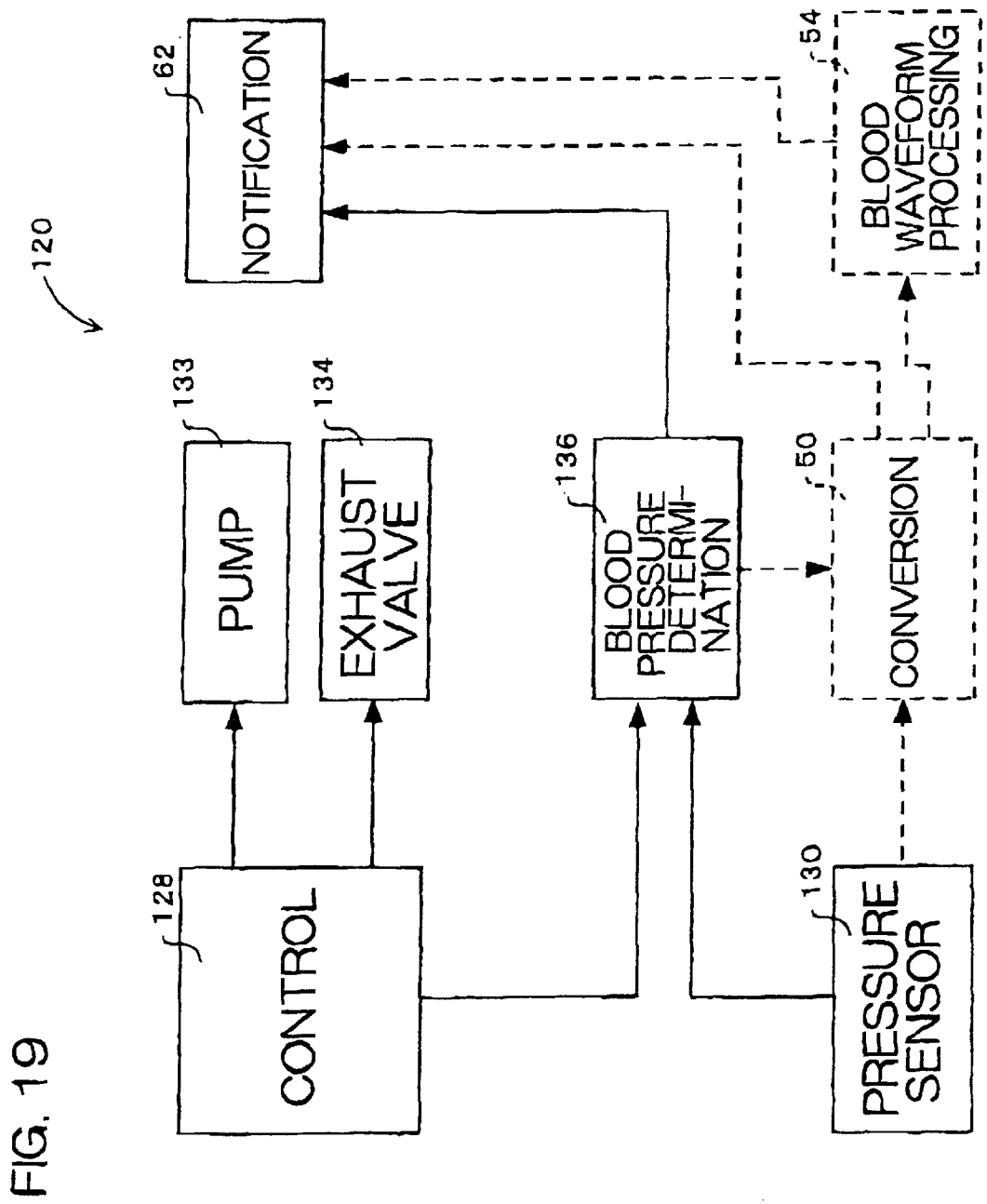
FIG. 19 is a block diagram showing the electric configuration of the blood pressure monitor of the fifth embodiment.

FIG. 19 is a block diagram showing the electric configuration of the blood pressure monitor 120 of this embodiment. As shown in this figure, the blood pressure monitor 120 is provided with a control section 128, a blood pressure determination section 136, and a notification section 62 in addition to the previously described sections.

The control section 128 controls operation of the pump 133 and the exhaust valve 132 so that the amount of fluid filled in the pressure applying section 124 can be adjusted so as to change the pressure applied by pressure applying section 124. In this manner, the pressure applied to the radial artery 94 by the artery pressing section 126 can be varied within the prescribed range. The control section 128 comprises, for example, a CPU and a memory which stores a program for operating the CPU.

The blood pressure determination section 136 takes information on various pressures applied by the artery pressing section 126 from the control section 128, and determines the maximum and minimum blood pressures based on the signals detected by the pressure sensor 130 at each of these various pressures. The blood pressure determination section 136 comprises, for example, a CPU and a memory which stores a program for operating the CPU.

The notification section 62 may comprise a display section which indicates the blood pressure values determined by the blood pressure determination section 136 as characters, a graph, or the like, such as an LCD, CRT, plotter, or printer, for example, or may comprise a sound creation section which indicates the blood pressure values by sound, such as a combination of a sound synthesizer and a speaker, for example.

5.2 Operation of Blood Pressure Monitor

The blood pressure monitor 120 operates as follows, for example, to measure blood pressure.

A cuff-like band 122 is wound around the wrist so that the artery pressing section 126 comes to a point corresponding to the radial artery 94.

The control section 128 controls operation of the pump 133 and the exhaust valve 134 so that the amount of fluid filled into the pressure applying section 124 can be adjusted so as to change the pressure applied by the pressure applying section 124. In this manner, the pressure applied to the radial artery 94 by the artery pressing section 126 can be varied within the prescribed range. Specifically, the pressure applied by the artery pressing section 126 is controlled by the control section 128 to a range slightly higher than the commonly encountered blood pressure, for example, in the range of 250 to 20 mmHg.

In each point pressed by the artery pressing section 126, the pressure sensor 130 which detects a vibration of the radial artery 94 detects signals corresponding to the vibration of the blood vessel walls due to the blood which flows through blood vessels constricted by the artery pressing section 126. The result for each pressure by the artery pressing section 126 is stored in the blood pressure determination section 136. Each pressing force value applied by the artery pressing section 126 is transmitted to the blood pressure determination section 136 from the control section 128 which controls the pressing force value.

In the same manner as in the first embodiment, the blood pressure determination section 136 determines the blood pressure when a sufficient number of pressure samples is obtained over the above-mentioned range for the artery pressing section 126.

The information on the maximum and minimum blood pressures thus determined is transmitted to the notification section 62, and presented by the notification section 62 as a display such as a numerical value or a graph, printed characters, or as a voice.

5.3 Modification of the Fifth Embodiment 5.3.1 In the above description, air was given as an example of the fluid filled into the pressure applying section 124. The fluid filled into the pressure applying section 124, however, may be other gases such as oxygen, nitrogen, helium, and argon, or may be a liquid such as water, mercury, alcohol, or oil. When a fluid other than air is used, a reservoir for storing such a fluid is necessary.

5.3.2 In the above embodiments, the radial artery 94 was taken as an example of artery to be pressed by the artery pressing section 126 for detection of pulse using the pressure sensor 130. However, the artery pressed by the artery pressing section 126 for detection of a vibration using the pressure sensor 130 is not limited to the radial artery, but may be any artery in the extremities and fingers such as the ulnar artery of the wrist, palmar finger artery, brachial artery, popliteal artery, and the like.

5.3.3 As shown in FIG. 19 in broken lines, the blood pressure monitor 120 may further comprise a conversion section 50 and a blood-pressure-waveform processing section 54.

The conversion section 50 converts signals detected by the pressure sensor 130 into a blood pressure waveform using the information on the maximum and minimum blood pressures determined by the blood pressure determination section 136. In the detection of signals used in this conversion by the pressure sensor 130, it is desirable that a pressure suitable for obtaining a signal waveform close to the blood pressure waveform from the pressure sensor 130 be applied to the artery pressing section 126 and pressure applying section 124. Specifically, it is desirable that the control section 128 control the pump 133 and the exhaust valve 134 so that such a pressure may be applied to the artery pressing section 126 and pressure applying section 124. In this manner, the blood pressure monitor 120 can obtain blood pressure waveforms non-invasively. The conversion section 50 comprises, for example, a CPU and a memory which stores a program for operating the CPU. Using this conversion section 50, the blood pressure monitor 120 can obtain blood pressure waveforms of the artery shown in FIG. 13, for example. General matters on the blood pressure waveform in the artery have been described in connection with the second embodiment in reference to FIG. 13.

Based on the blood pressure waveform obtained by the conversion section 50, the blood-pressure-waveform processing section 54 calculates at least one of the following items: a mean blood pressure $BP_{mean}$, a pulse pressure $\Delta BP$ which is the difference between the maximum and minimum blood pressures, an after-ejection pressure $\Delta BP_P$ which is the pressure difference between the dicrotic notch and the maximum blood pressure, a dicrotic wave height $\Delta BP_D$ which is the pressure difference between the dicrotic notch and the dicrotic wave peak, an after-ejection pressure ratio $\Delta BP_P/\Delta BP$ which is the after-ejection pressure $\Delta BP_P$ normalized by the pulse pressure $\Delta BP$, and a dicrotic wave height after-ejection pressure ratio $\Delta BP_D/\Delta BP_P$ which is a ratio of the dicrotic wave height $\Delta BP_D$ and the after-ejection pressure $\Delta BP_P$.

Data concerning blood pressure waveforms in the artery obtained by the conversion section 50 and the above-mentioned various indices on blood pressure waveforms obtained by the blood-pressure-waveform processing section 54 are transmitted to the notification section 62, and presented by the notification section 62 as a display such as a numerical value or a graph, printed characters, or as a voice.

5.4 Effects of the Fifth Embodiment

In the blood pressure monitor 120 of this embodiment, the artery pressing section 126 installed in the pressure applying section 124 located inside the band 122 locally presses the artery at various pressures. The blood pressure determination section 136 determines the maximum and minimum pressures based on the various pressing force values applied and the signals detected by the pressure sensor 130 at these various pressing force values. Therefore, the artery is pressed by the artery pressing section 126 at a sufficient pressure so that the region in which the pressure applying section 124 or the band 122 come into contact may not become so large. As a result, a pressure so great as to impart an unpleasant or disagreeable feeling to the subject will not be applied.

In addition, because the artery pressing section 126 only locally presses the artery, the pressing operation will not be interfered with by the sinews or bones which may be present close to the artery Therefore, the pressing operation can press the artery with certainty, ensuring measurement of the blood pressure more accurately than in the conventional method in which the artery is directly pressed by a cuff or the like applied to the circumference of the extremities or fingers. Thus, more accurate blood pressure measurement can be ensured.

In addition, the use of the band 122 similar to cuffs commonly used for blood pressure measurement and the pressure applying section 124 allows the blood pressure monitor 120 of this embodiment to be designed as a comparatively small instrument.

6. Sixth Embodiment

The blood pressure monitor of the sixth embodiment is almost the same as that of the fifth embodiment, except that the former is a blood pressure monitor for use on the section in which the major arteries which are the first and second arteries exist comparatively near the skin, wherein the pressure applying section applies a pressure directly to the first artery and the pressure sensor detects the vibration of the first artery conveyed through the pressure applying section as a pressure change. Another difference is that the pressure applying section is equipped with a second artery pressing section which presses the second artery to substantially shut off the blood flow. Other features are the same as in the fifth embodiment, so description thereof is omitted. Corresponding sections in each figure are indicated by the same symbols as in the first embodiment.

6.1 Configuration of Blood Pressure Monitor

Figure 20:
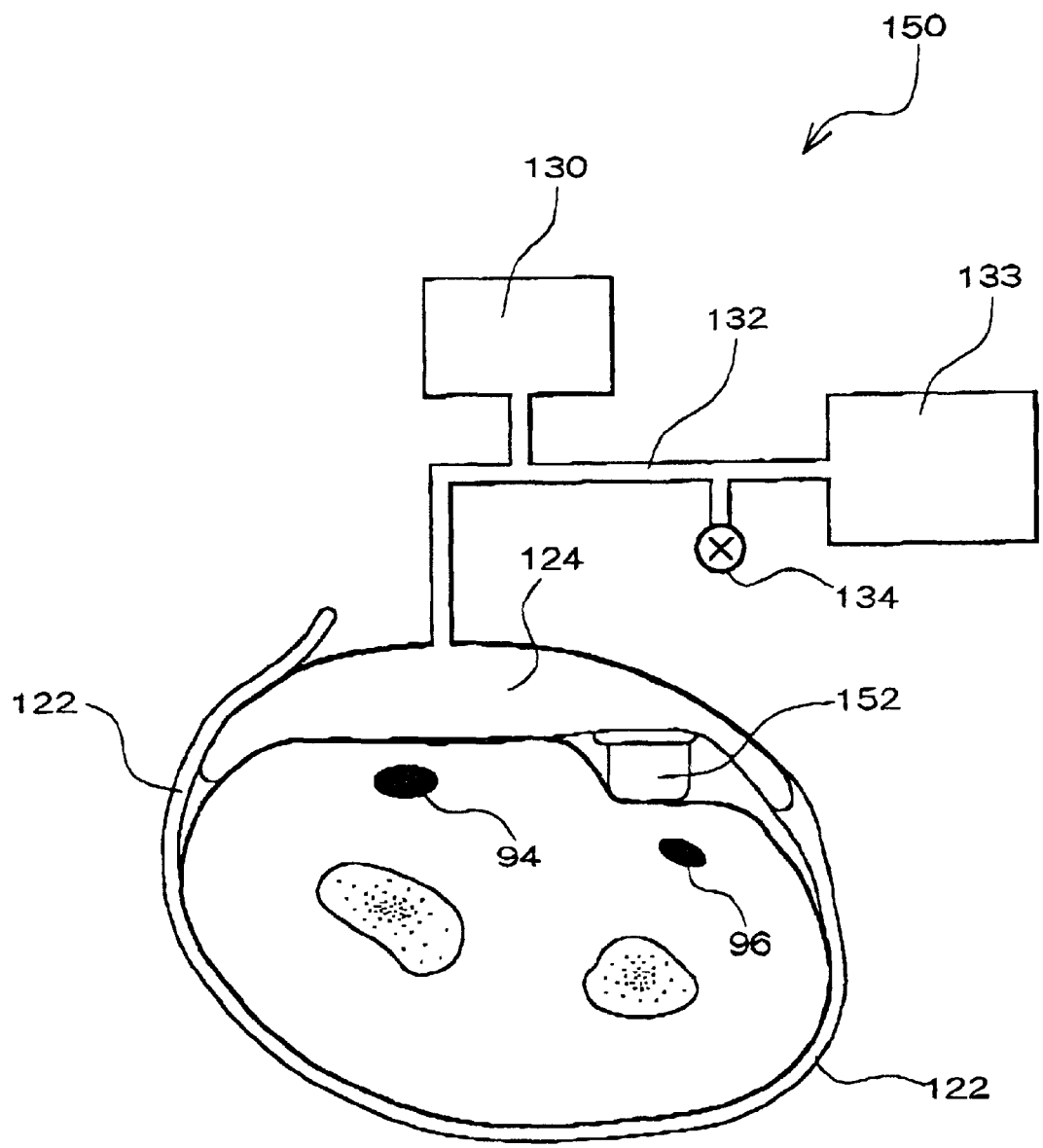
FIG. 20 is a schematic view showing blood pressure measurement using the blood pressure monitor of a sixth embodiment worn on the wrist.

FIG. 20 is a schematic view showing blood pressure measurement using a blood pressure monitor 150 of this embodiment worn on the wrist. As shown in the figure, the blood pressure monitor 150 of this embodiment is provided with a second artery pressing section 152 projecting from the pressure applying section 124 and is wound around the wrist so that the second artery pressing section 152 may be located on the point corresponding to the ulnar artery 96 as the second artery. The second artery pressing section 152 is designed so as to locally press the ulnar artery 96 to substantially shut off or restrict blood flow therein. In addition, the pressure applying section 124 directly contacts and presses the skin above the radial artery 94 as the first artery.

The pressure sensor 130 can detect a vibration of the radial artery 94 which is conveyed as a fluid pressure change via the pressure applying section 124. Specifically, because the pressure applying section 124 located above the radial artery 94 applies pressure according to the vibration of the radial artery 94, the fluid pressure in the pressure applying section 124 changes according to the vibration of the radial artery 94. Accordingly, the pressure sensor 130 which detects such a pressure change can output signals corresponding to the vibration of the radial artery 94. When the pressure sensor 130 detects a vibration from the radial artery 94, the second artery pressing section 152 presses the ulnar artery 96 to substantially shut off the blood flow therein.

The electric configuration of the blood pressure monitor 120 of this embodiment is the same as that of the fifth embodiment shown as a block diagram in FIG. 19. The control section 128 controls operation of the pump 133 and the exhaust valve 132 so that the amount of the fluid filled into the pressure applying section 124 can be adjusted so as to vary the pressure applied to the radial artery 94 within the prescribed range.

6.2 Operation of Blood Pressure Monitor

The blood pressure monitor 120 operates as follows, for example, to measure blood pressure.

A cuff-like band 122 is wound around the wrist so that the second artery pressing section 152 comes to a point corresponding to the ulnar artery 96.

The control section 128 controls operation of the pump 133 and the exhaust valve 134 so that the amount of fluid filled into the pressure applying section 124 can be adjusted so as to change the pressure applied by the pressure applying section 124. In this manner, the pressure applied to the radial artery 94 by the pressure applying section 124 can be varied within the prescribed range. Specifically, the pressure applied by the pressure applying section 124 is controlled by the control section 128 to a range slightly higher than the commonly encountered blood pressure, for example, in the range of 250 to 20 mmHg. In this pressure range, the second artery pressing section 152 installed in the pressure applying section 124 presses the ulnar artery 96 to substantially shut off the blood flow therein.

In each point pressed by the pressure applying section 124, the pressure sensor 130 which detects a vibration of the radial artery 94 detects signals corresponding to the vibration of the blood vessel walls due to the blood which flows through blood vessels constricted by the pressure of the pressure applying section 124. The result for each pressure by the pressure applying section 124 is stored in blood pressure determination section 136. Each pressing force value applied by the pressure applying section 124 is transmitted to the blood pressure determination section 136 from the control section 128 which controls the pressing force value.

In the same manner as in the first embodiment, the blood pressure determination section 136 determines the blood pressure when a sufficient number of pressure samples is obtained over the above-mentioned range for the pressure applying section 124. The result is reported by the notification section 62.

6.3 Modification of the Sixth Embodiment 6.3.1 In the above embodiments, the radial artery 94 was taken as an example of the first artery to be pressed by the artery pressing section 124 for detection of a vibration using the pressure sensor 130, and the ulnar artery 96 as an example of the second artery to be pressed by the second artery pressing section 152. However, the first artery which is pressed by the artery pressing section 124 for detection of a vibration using the pressure sensor 130 may be the ulnar artery 96, and the second artery which is pressed by the second artery pressing section 152 may be the radial artery 94. Furthermore, in measuring blood pressure at any other portion of the extremities or fingers in which two arteries flow comparatively close to the skin, it is possible to modify the blood pressure monitor 150 so that either one of the two arteries as the first artery may be pressed by the artery pressing section 124 for detection of a vibration using the pressure sensor 130, and the other artery may be pressed by the second artery pressing section 152.

6.3.2 The modification described for the fifth embodiment can be applied also to this embodiment.

6.3.3 As described in 5.3.3 relating to the modification for the fifth embodiment, the blood pressure monitor 150 of this embodiment may further comprise a conversion section 50 and a blood-pressure-waveform processing section 54.

6.4 Effects of the Sixth Embodiment

Because this blood pressure monitor 150 is equipped with the second artery pressing section 152 which locally presses the second artery, the blood pressure monitor can substantially shut off the blood flow to the peripheral side from the pressed point. Therefore, the signals from the first artery detected by the pressure sensor 130 will not be affected by the pulses due to the blood flowing from the second artery via the artery which connect the second and first arteries, thereby ensuring more accurate blood pressure measurement.

In the blood pressure monitor 150 of this embodiment, because the second artery pressing section 152 locally presses the second artery, there will be no risk of nerves or the like around the second artery being strongly pressed, thus minimizing any unpleasant or disagreeable feeling imparted to the subject.

In addition, the use of the band 122 similar to cuffs commonly used for blood pressure measurement and the pressure applying section 124 allows the blood pressure monitor 150 of this embodiment to be designed as a comparatively small instrument.

7. Seventh Embodiment

The blood pressure monitor of the seventh embodiment is almost the same as that of the fifth embodiment, except that the former is a blood pressure monitor for use in the section in which the two major arteries which are the first and second arteries exist comparatively near the skin. Thus, the blood pressure monitor of this embodiment differs from that of the fifth embodiment in that the former has no pressure applying section of a size covering the first and second arteries, is provided with first and second artery pressing sections which press the arteries by expansion of the fluid enclosed therein, and provided with a tube equipped with a valve which allows the tube to be connected only with the second artery pressing section. Other features are the same as in the fifth embodiment, so description thereof is omitted. Corresponding sections in each figure are indicated by the same symbols as in the first embodiment.

7.1 Configuration of Blood Pressure Monitor

Figure 21:
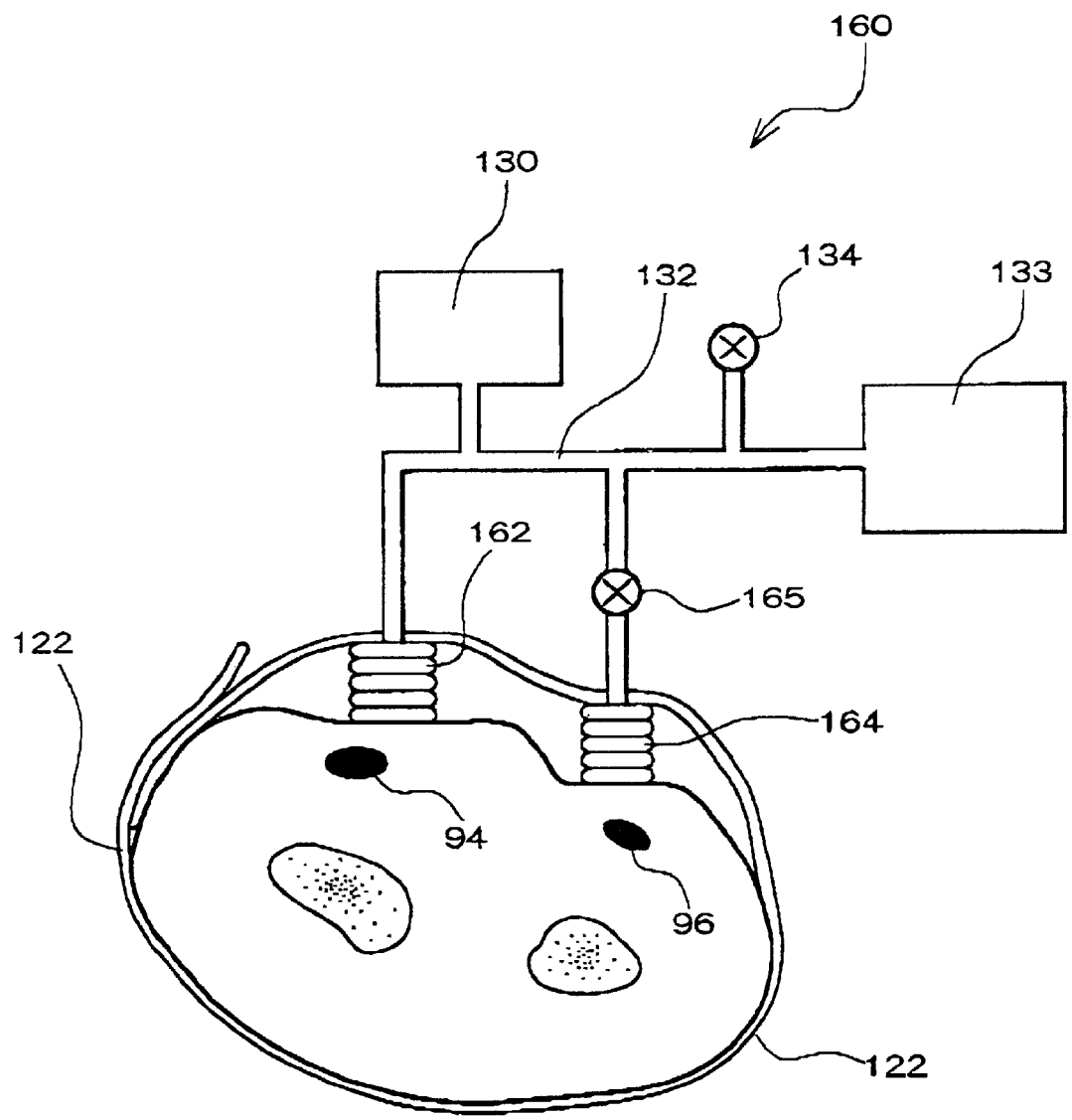
FIG. 21 is a schematic view showing blood pressure measurement using the blood pressure monitor of a seven embodiment worn on the wrist.

FIG. 21 is a schematic view showing blood pressure measurement using a blood pressure monitor 160 of this embodiment worn on the wrist. As shown in this figure, the blood pressure monitor 160 of this embodiment is provided with a first artery pressing section 162 which locally presses the radial artery 94 as the first artery and a second artery pressing section 164 which locally presses the ulnar artery 96 as the second artery. These are directly attached to the blood pressure monitor via a band 122. The first artery pressing section 162 and the second artery pressing section 164 are individually connected to a tube 132. A valve 165 which allows or interrupts fluid flow therein is provided in part of the tube 132 connected with the second artery pressing section.

A pressure sensor 130 is provided so that it can detect a vibration of the radial artery 94 which is conveyed as a fluid pressure change via the first artery pressing section 162 when the valve 165 is closed.

Figure 22:
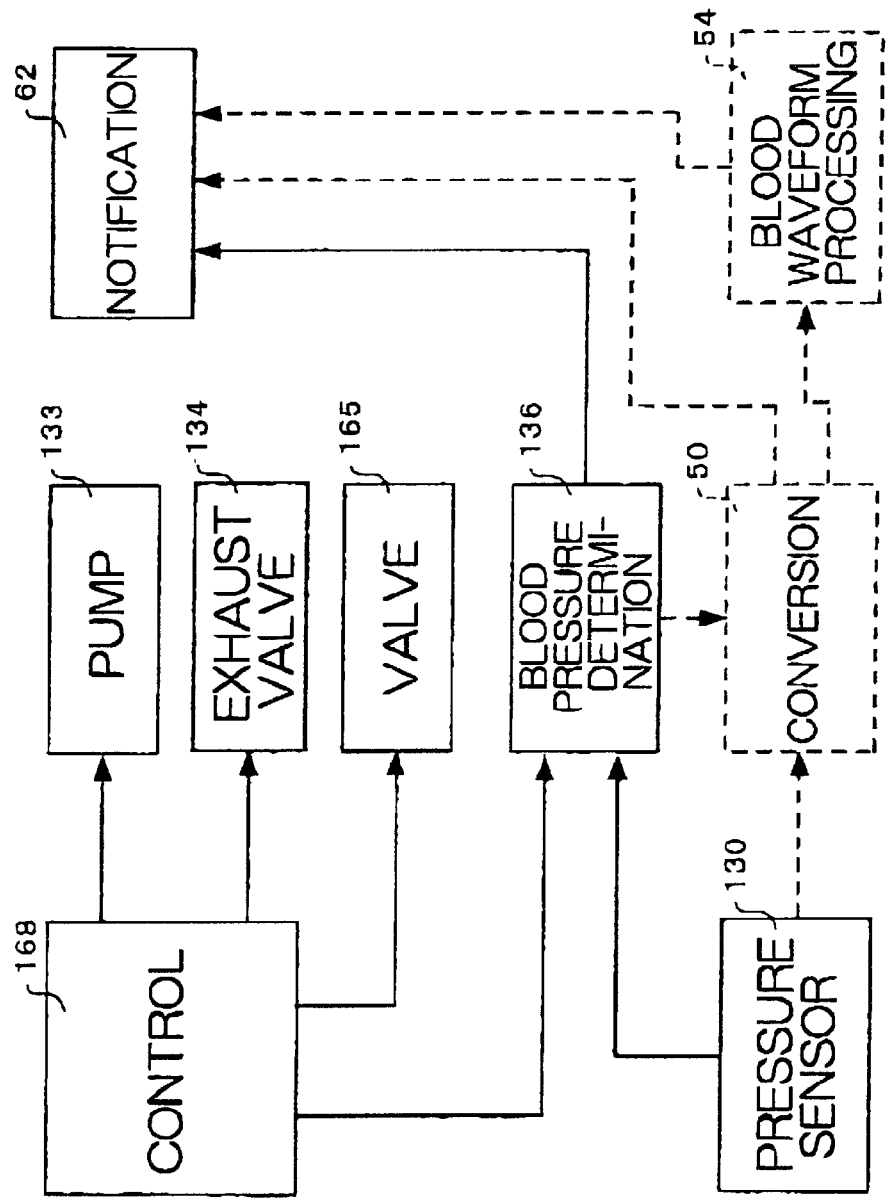
FIG. 22 is a block diagram showing the electric configuration of the blood pressure monitor of the seventh embodiment.

The electric configuration of the blood pressure monitor 160 of this embodiment is shown in the block diagram of FIG. 22, which differs from that of the fifth embodiment in that the control section 168 has an additional function of controlling the valve 165 provided only in part of the tube 132 connected with the second artery pressing section 164. The control section 168 controls operation of the pump 133, the exhaust valve 132, and the valve 165 so that the amount of fluid filled into the first artery pressing section 162 may be adjusted so as to vary the pressure applied to the radial artery 94 within the prescribed range.

7.2 Operation of Blood Pressure Monitor

The blood pressure monitor 160 operates as follows, for example, to measure blood pressure.

First, a cuff-like band 122 is wound around the wrist so that the first artery pressing section 162 comes to a point corresponding to the radial artery 94, and the second artery pressing section 164 to the ulnar artery 96.

The control section 168 controls operation of the pump 133 and the exhaust valve 134 so that the amount of fluid filled into the second artery pressing section 164 can be adjusted so as to change the pressure applied by the second artery pressing section 164 to a degree to substantially shut off the blood flowing through the ulnar artery 96. The pressure applied by the second artery pressing section 164 to substantially shut off the blood flowing in the ulnar artery 96 can be controlled by the control section 168 to close the valve 165.

The control section 168 also controls operation of the pump 133 and the exhaust valve 134 so that the amount of the fluid filled into the first artery pressing section 162 can be adjusted so as to vary the pressure applied to the radial artery 94 by the first artery pressing section 162 within the prescribed range. Specifically, the pressure applied by the first artery pressing section 162 is controlled by the control section 168 to a range slightly higher than the commonly encountered blood pressure, for example, in the range of 250 to 20 mmHg.

In each point pressed by the first artery pressing section 162, the pressure sensor 130 which detects a vibration of the radial artery 94 detects signals corresponding to the vibration of the blood vessel walls due to the blood which flows through blood vessels constricted by the first artery pressing section 162. The result for each pressure by the first artery pressing section 162 is stored in the blood pressure determination section 136. Each pressing force value applied by the first artery pressing section 162 is transmitted to the blood pressure determination section 136 from the control section 168 which controls the pressing force value.

In the same manner as in the first embodiment, the blood pressure decision section 136 determines the blood pressure when a sufficient number of pressure samples is obtained over the above-mentioned range for the first artery pressing section 162. The result is reported by the notification section 62.

7.3 Modification of the Seventh Embodiment 7.3.1 In the above embodiments, the radial artery 94 was taken as an example of the first artery to be pressed by the first artery pressing section 162 for detection of a vibration using the pressure sensor 130, and the ulnar artery 96 as an example of the second artery to be pressed by the second artery pressing section 164. However, the first artery which is pressed by the first artery pressing section 162 for detection of a vibration using the pressure sensor 130 may be the ulnar artery 96, and the second artery which is pressed by the second artery pressing section may be the radial artery 94. Furthermore, in measuring blood pressure at any other portion of the extremities or fingers in which two arteries flow comparatively close to the skin, it is possible to modify the blood pressure monitor 160 so that either one of the two arteries as the first artery may be pressed by the first artery pressing section 162 for detection of a vibration using the pressure sensor 130, and the other artery may be pressed by the second artery pressing section 164.

7.3.2 The modification described in 5.3.1 for the fifth embodiment can be applied also to this embodiment.

7.3.3 As described in 5.3.3 relating to the modification for the fifth embodiment, the blood pressure monitor 160 of this embodiment may further comprise a conversion section 50 and a blood-pressure-waveform processing section 54. The blood pressure monitor 160 having the conversion section 50 and the blood-pressure-waveform processing section 54 may further comprise the sections indicated by broken lines in FIG. 22.

7.4 Effects of the Seventh Embodiment

In the blood pressure monitor 160 of this embodiment, the first artery pressing section 162 and the second artery pressing section 164 installed inside the band 122 locally press the arteries 94 and 96. Therefore, the arteries 94 and 96 are pressed by the artery pressing sections 162 and 164 at a sufficient pressure so that the pressure applied to the region facing the band 122 may not become so large. As a result, a pressure sufficiently great as to impart an unpleasant or disagreeable feeling to the subject will not be applied.

In addition, because the first artery pressing section 162 and the second artery pressing section 164 only locally press the arteries 94, 96, the pressing operation by the first artery pressing section 94 and the second artery pressing section 96 will not be interfered with by the sinews or bones which may be present close to these arteries 94, 96. Therefore, the pressing operation can press the artery with certainty, ensuring measurement of the blood pressure more accurately than in the conventional method in which the arteries are directly pressed by a cuff or the like applied to the circumference of the extremities or fingers. Thus, more accurate blood pressure measurement can be ensured.

In addition, the use of the band 122 similar to cuffs commonly used for blood pressure measurement allows the blood pressure monitor 160 of this embodiment to be designed as a comparatively small instrument.

Furthermore, because this blood pressure monitor 160 is equipped with the second artery pressing section 164 which locally presses the ulnar artery 96, the blood pressure monitor can substantially shut off the blood flow to the peripheral side from the pressed point. Therefore, the signals from the radial artery 94 detected by the pressure sensor 130 will not be affected by the pulses due to the blood flowing from the ulnar artery 96 via the artery and the like which connect the radial artery 94 and the ulnar artery 96, thereby ensuring more accurate blood pressure measurement.

8. Eighth Embodiment

The blood pressure monitor of the eighth embodiment is almost the same as that of the fifth embodiment, except that the former does not have the artery pressing section 126 and the control section employs a different controlling method. Other features are the same as in the fifth embodiment, so description thereof is omitted. Corresponding sections in each figure are indicated by the same symbols as in the first embodiment.

8.1 Configuration of Blood Pressure Monitor

Figure 23:
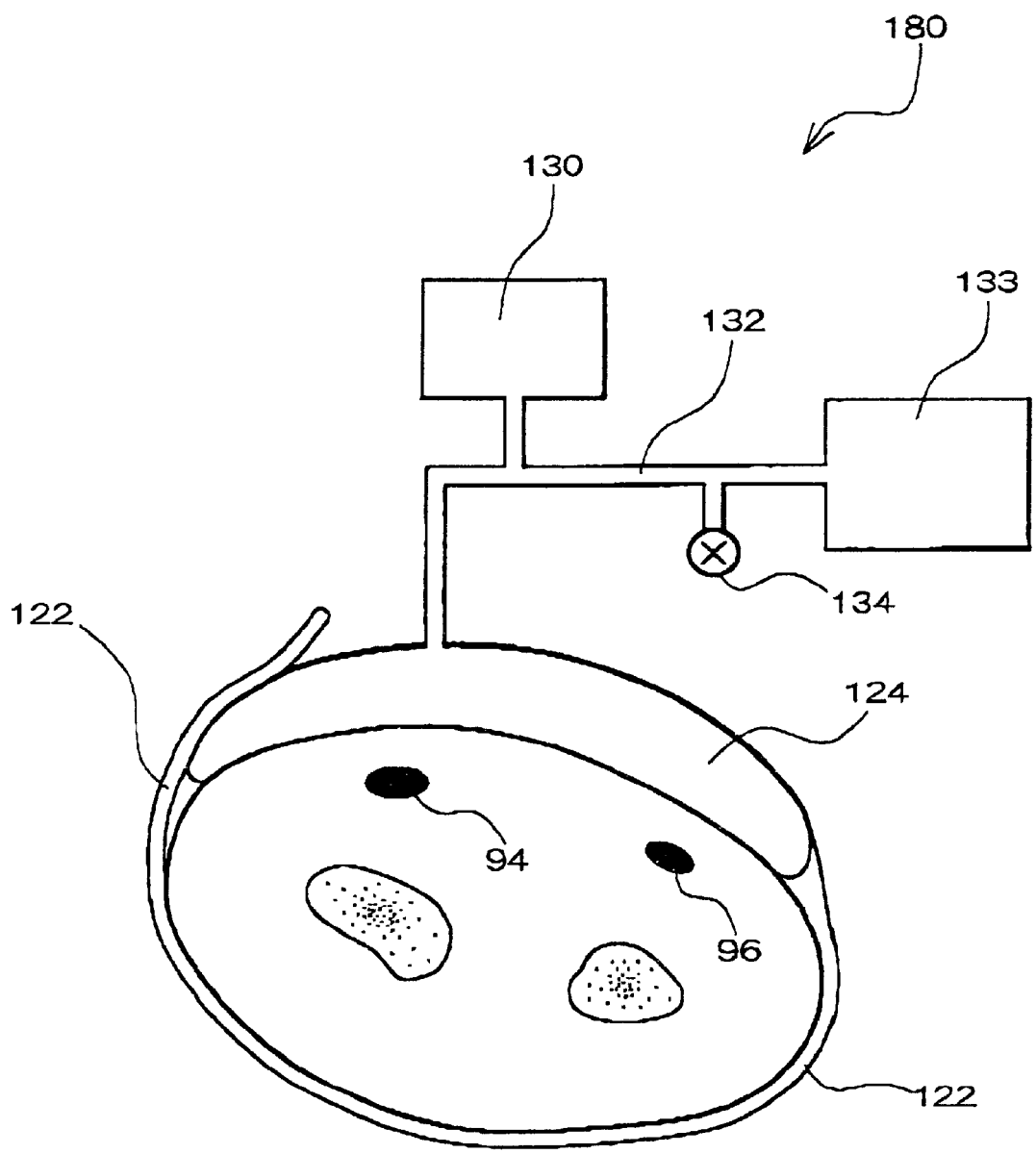
FIG. 23 is a schematic view showing blood pressure measurement using the blood pressure monitor of an eighth embodiment worn on the wrist.

FIG. 23 is a schematic view showing blood pressure measurement using a blood pressure monitor 180 of this embodiment worn on the wrist. As shown in this figure, the blood pressure monitor 180 of this embodiment is formed so that a pressure applying section 124 acting as an artery pressing section directly presses the radial artery 94 and the ulnar artery 96.

The pressure sensor 130 can detect a vibration of the radial artery 94 and the ulnar artery 96 which is conveyed as a fluid pressure change via the pressure applying section 124 acting as an artery pressing section. specifically, because the pressure applying section 124 located above the radial artery 94 and the ulnar artery 96 applies pressure according to the vibration of the radial artery 94 and the ulnar artery 96, the fluid pressure in the pressure applying section 124 changes according to the vibration of the radial artery 94 and the ulnar artery 96. Accordingly, the pressure sensor 130 which detects such a pressure change can output signals corresponding to the vibration of the radial artery 94 and the ulnar artery 96.

The electric configuration of the blood pressure monitor 180 of this embodiment is the same as that of the fifth embodiment shown as a block diagram in FIG. 19. The control section 128 controls operation of the pump 133 and the exhaust valve 132 so that the amount of the fluid filled into the pressure applying section 124 can be adjusted so as to gradually increase the pressure applied to the radial artery 94 and the ulnar artery 96 from the prescribed minimum pressure.

8.2 Operation of Blood Pressure Monitor

The blood pressure monitor 120 operates as follows, for example, to measure blood pressure.

A cuff-like band 122 is wound around the wrist so that the pressure applying section 124 as an artery pressing section comes to the point corresponding to the ulnar artery 96 and the ulnar artery 96.

Figure 24:
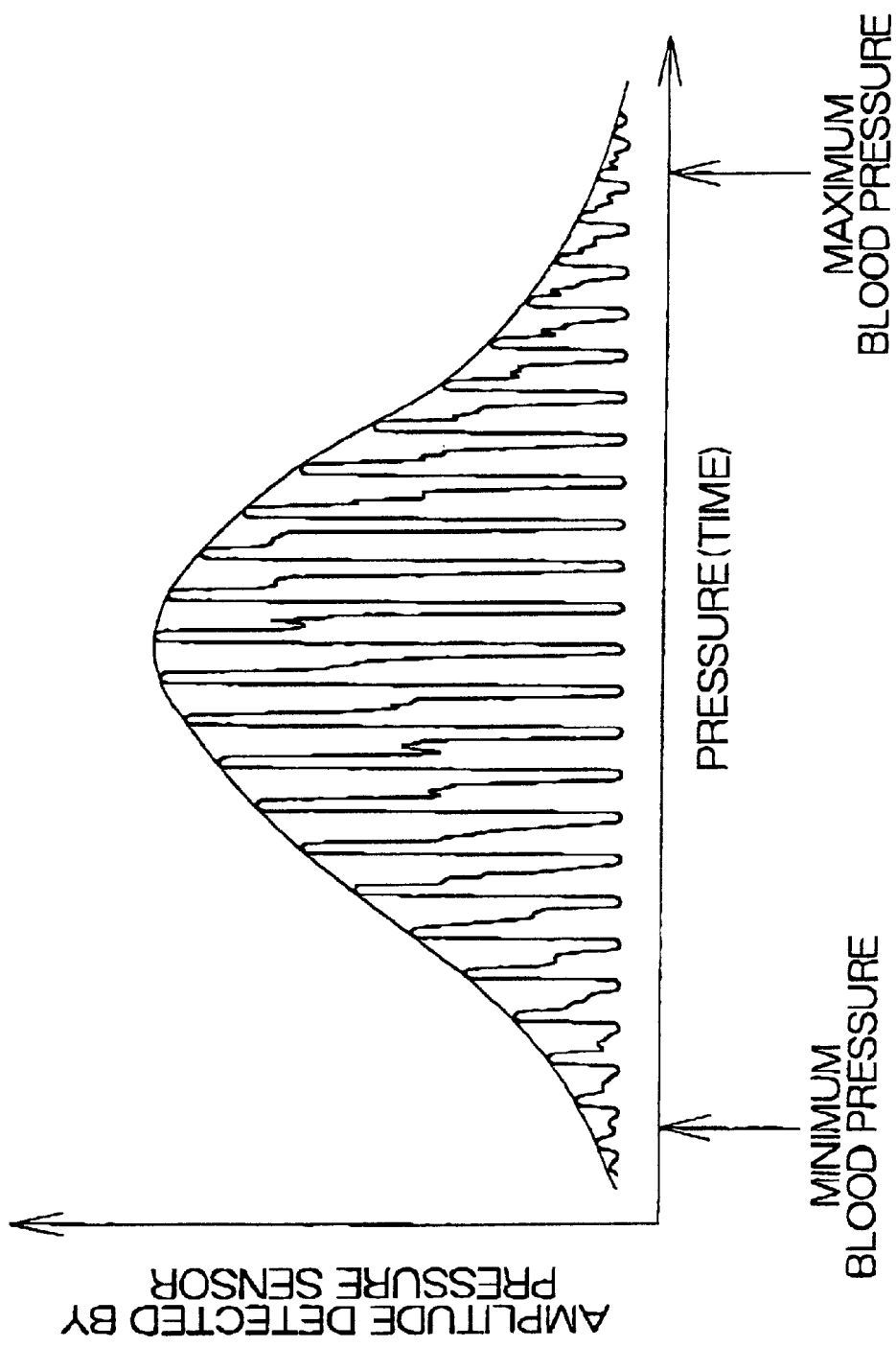
FIG. 24 is a graph schematically showing the relationship between the pressure applied by a pressure applying section and signals detected by a pressure sensor.

Next, the control section 128 controls operation of the pump 133 and the exhaust valve 134 so that the amount of the fluid filled into the pressure applying section 124 can be adjusted so as to change the pressure applied by the pressure applying section 124. In this manner, the pressure applied to the radial artery 94 and the ulnar artery 96 by the pressure applying section 124 may be gradually increased from a pressure significantly lower than the commonly encountered minimum blood pressure, for example, 20 mmHg In each point pressed by the artery pressing section 124, the pressure sensor 130 which detects a vibration of the radial artery 94 and the ulnar artery 96 detects signals corresponding to the vibration of the blood which flows through blood vessels. The signals detected by the pressure sensor 130 at each pressure applied by the pressure applying section 124 will be read by the blood pressure determination section 136 together with the pressure of the pressure applying section 124 from time to time. If the pressure applied by the pressure applying section 124 is controlled as mentioned above, the signals detected by the pressure sensor 130 are converted into signals consisting of a static pressure (direct component) which corresponds to the pressure applied by the pressure applying section 124 and a kinetic pressure (alternating component) which corresponds to the vibration of the blood vessel walls due to blood flow. FIG. 24 is a graph schematically showing the kinetic pressure (alternating component) which corresponds to the vibration of the blood vessel walls due to blood flow as an amplitude characteristic to the pressure applied by the pressure applying section 124, when the pressure applied by the pressure applying section 124 is controlled as mentioned above. As can be seen from the figure, the amplitude of the pressure fluctuation wave detected by the pressure sensor in response to vascular vibration becomes negligible when the pressure applied by the pressure applying section 124 is less than the minimum blood pressure or more than the maximum blood pressure, even though such an amplitude may not become zero due to noise or other factors.

Making use of such characteristics, the pressure applied by the pressure applying section 124 at the point where the pressure sensor 130 begins to detect vascular vibration due to the blood flowing in the blood vessels constricted by pressure from the pressure applying section 124 is stored in the pressure applying section 124 as the minimum pressure in this blood pressure monitor 180.

Next, the pressure applied by the pressure applying section 124 immediately before the point where the pressure sensor 130 stops detection of vascular vibration due to the blood flowing in the blood vessels constricted by the pressure of the pressure applying section 124 is stored in the pressure applying section 124 as the maximum pressure, whereupon the blood pressure measuring operation is completed.

8.3 Modification of the Eighth Embodiment 8.3.1 Although the radial artery 94 and the ulnar artery 96 were given as the artery to be pressed by the pressure applying section 124 as an artery pressing section for detection of a vibration using the pressure sensor 130 in the above description, it is possible that the artery pressed by the pressure applying section 124 as an artery pressing section for detection of a vibration using the pressure sensor 130 may be either the radial artery 94 or the ulnar artery 96. The blood pressure monitor 180 of this embodiment may further be modified so that the artery pressed by the pressure applying section 124 as an artery pressing section for detection of a vibration using the pressure sensor 130 may be other artery at any other portion of the extremities or fingers.

8.3.2 The method of controlling the pressure applied to the artery by the pressure applying section 124 (the artery pressing section) by the control section 128 in the blood pressure monitor 180 of this embodiment, that is, the controlling method of gradually increasing the pressure from a level lower than the minimum blood pressure to a level almost equivalent to the maximum pressure can be applied to the blood pressure monitors in the previously described embodiments. This controlling method can decrease maximum pressure applied to the artery pressing section as compared with conventional blood pressure monitors in which a pressure higher than the conceivable maximum pressure is first applied and then gradually decreased. As a result, the risk of imparting an unpleasant or disagreeable feeling to the subject due to application of an unduly great pressure can be avoided.

8.3.3 The modification described in 5.3.1 for the fifth embodiment can also be applied to this embodiment.

8.3.4 As described in 5.3.3 relating to the modification for the fifth embodiment, the blood pressure monitor 180 of this embodiment may further comprise a conversion section 50 and a blood-pressure-waveform processing section 54.

8.4 Effects of the Eighth Embodiment

In the blood pressure monitor 180 of this embodiment, the control section 128 controls the pressure applied to the artery by the pressure applying section 124 as an artery pressing section so that this pressure may be gradually increased from the prescribed minimum pressure. In each step of the pressure increase, the blood pressure determination section 136 determines the blood pressure based on signals detected by the pressure sensor 130 and the pressure data stored therein from time to time taken at the time of blood pressure determination. Specifically, in the blood pressure measurement using this blood pressure monitor 180, the pressure applied by the pressure applying section 124 at the point where the pressure sensor 130 begins to detect vascular vibration due to the blood flowing in the blood vessels constricted by the pressure of the pressure applying section 124 is stored in the pressure applying section 124 as the minimum pressure, while the pressure lower than the conceivable minimum pressure which is first applied is gradually increased. Then, the pressure applied by the pressure applying section 124 immediately before the point where the pressure sensor 130 stops detecting vascular vibration due to the blood flowing in the blood vessels constricted by the pressure of the pressure applying section 124 is stored in the pressure applying section 124 as the maximum pressure, whereupon the blood pressure measuring operation is completed.

In this manner, blood pressure measurement using the blood pressure monitor 180 of this embodiment can be completed at the moment when the pressure applied by the pressure applying section 124 almost becomes the maximum blood pressure. Therefore, it is possible to decrease the maximum pressure applied to the pressure applying section 124 as compared with conventional blood pressure monitors in which a pressure higher than the conceivable maximum pressure is first applied and then gradually decreased. As a result, a pressure sufficiently great as to impart an unpleasant or disagreeable feeling to the subject will not be applied.

In conventional blood pressure monitors in which a pressure higher than the commonly encountered maximum pressure is first applied and then gradually decreased, a process for decreasing the pressure applied by the pressure applying section to a low level is necessary after a process of increasing the pressure of the pressure applying section to a high level. In contrast, because it is possible to measure the blood pressure -in a single process of increasing the pressure of the pressure applying section 124, the blood pressure monitor 180 of this embodiment can reduce the time for the measurement as compared with the conventional blood pressure monitors in which a pressure higher than the commonly encountered maximum pressure is first applied and then gradually decreased.

The present invention is not limited to the embodiments described above. Many modifications and variations are possible without departing from the spirit and scope of the present invention .

What is claimed is:

1. A blood pressure monitor comprising:
an artery pressing section adapted to locally press an artery of any one of extremities and fingers at an arbitrarily variable pressing force;
a control section which controls the pressing force applied by the artery pressing section;
a vibration sensor for detecting a vibration of the artery at a point on the peripheral side of the point to be pressed by the artery pressing section; and
a blood pressure determination section which determines a maximum blood pressure and a minimum blood pressure based on various pressing force values applied by the artery pressing section and signals detected by the vibration sensor at the various pressing force values.

2. The blood pressure monitor according to claim 1, further comprising a positioning mechanism which positions the artery pressing section and the vibration sensor on the artery.

3. The blood pressure monitor according to claim 1, further comprising guides provided on each side of the vibration sensor and guiding the vibration sensor to the artery by being located on both sides of the artery.

4. The blood pressure monitor according to claim 1, further comprising a peripheral side pressing section which presses the artery at a point peripheral to the vibration sensor and almost completely shuts off the vibration transmitted by an artery section peripheral to the vibration sensor.

5. The blood pressure monitor according to claim 1, wherein the vibration sensor detects the vibration transmitted to the artery pressing section.

6. The blood pressure monitor according to claim 1, further comprising a sensor pressing section which causes the vibration sensor to press the artery.

7. The blood pressure monitor according to claim 1,
wherein the vibration sensor is a pulse wave sensor detecting a pulse waveform, and
wherein the blood pressure monitor further comprises a conversion section which converts the pulse waveform into a blood pressure waveform based on the maximum blood pressure and the minimum blood pressure.

8. The blood pressure monitor according to claim 7, further comprising a blood-pressure-waveform processing section which calculates at least one of following items based on the blood pressure waveform obtained by the conversion section; a mean blood pressure, a pulse pressure which is a difference between the maximum blood pressure and the minimum blood pressure, an after-ejection pressure which is a pressure difference between a dicrotic notch and the maximum blood pressure, a dicrotic wave height which is a pressure difference between the dicrotic notch and a dicrotic wave peak, an after-ejection pressure ratio which is the after-ejection pressure normalized by the pulse pressure, a dicrotic wave height ratio which is the dicrotic wave height normalized by the pulse pressure, and a dicrotic wave height after-ejection pressure ratio which is a ratio of the dicrotic wave height and the after-ejection pressure.

9. The blood pressure monitor according to claim 1,
wherein the artery pressed by the artery pressing section, of which vibration is detected by the vibration sensor, is a radial artery.

10. A blood pressure monitor comprising:
a first artery pressing section adapted to locally press a first artery of any one of extremities and fingers having the first artery and a second artery at an arbitrarily variable pressing force;
a control section which controls the pressing force applied by the first artery pressing section;
a second artery pressing section adapted to locally press the second artery;
a vibration sensor for detecting a vibration of the first artery at a pressed point or on a peripheral side thereof; and
a blood pressure determination section which determines a maximum blood pressure and a minimum blood pressure based on various pressing force values applied by the first artery pressing section and a signal detected by the vibration sensor at each of the pressing force values.

11. The blood pressure monitor according to claim 10, further comprising a positioning mechanism which positions the first artery pressing section and the vibration sensor on the first artery.

12. The blood pressure monitor according to claim 10, further comprising guides provided on each side of the vibration sensor and guiding the vibration sensor to the first artery by being located on both sides of the first artery.

13. The blood pressure monitor according to claim 10,
wherein the vibration sensor detects the vibration transmitted to the first artery pressing section.

14. The blood pressure monitor according to claim 10, further comprising a sensor pressing section which causes the vibration sensor to press the first artery.

15. The blood pressure monitor according to claim 10,
wherein the first artery pressed by the first artery pressing section, of which vibration is detected by the vibration sensor, is a radial artery.

16. The blood pressure monitor according to claim 10,
wherein the vibration sensor is a pulse wave sensor detecting a pulse waveform, and
wherein the blood pressure monitor further comprises a conversion section which converts the pulse waveforms into a blood pressure waveform based on the maximum blood pressure and the minimum blood pressure.

17. The blood pressure monitor according to claim 16, further comprising a blood-pressure-waveform processing section which calculates at least one of following items based on the blood pressure waveform obtained by the conversion section: a mean blood pressure, a pulse pressure which is a difference between the maximum blood pressure and the minimum blood pressure, a after-ejection pressure which is a pressure difference between a dicrotic notch and the maximum blood pressure, a dicrotic wave height which is a pressure difference between the dicrotic notch and a dicrotic wave peak, an after-ejection pressure ratio which is the after-ejection pressure normalized by the pulse pressure, a dicrotic wave height ratio which is the dicrotic wave height normalized by the pulse pressure, and a dicrotic wave height after-ejection pressure ratio which is a ratio of the dicrotic wave height and the after-ejection pressure.

18. A pulse wave detection apparatus comprising:
an artery pressing section adapted to locally press an artery of any one of extremities and fingers at an arbitrarily variable pressing force;
a control section which controls the pressing force applied by the artery pressing section; and
a pulse sensor for detecting a pulse of the artery at a peripheral side from where the artery pressing section is to press.

19. The pulse wave detection apparatus according to claim 18, further comprising a positioning mechanism which positions the artery pressing section and the pulse sensor on the artery.

20. The pulse wave detection apparatus according to claim 18, further comprising guides provided on each side of the pulse sensor and guiding the pulse sensor to the artery by being located on both sides of the artery.

21. The pulse wave detection apparatus according to claim 18,
wherein the pulse sensor detects the vibration transmitted to the artery pressing section.

22. The pulse wave detection apparatus according to claim 18, further comprising a sensor pressing section which causes the pulse sensor to press the artery.

23. The pulse wave detection apparatus according to claim 18,
wherein the artery pressed by the artery pressing section, of which pulse is detected by the pulse sensor, is a radial artery.

24. A pulse wave detection apparatus comprising:
an artery pressing section adapted to locally press an artery of any one of extremities and fingers at an arbitrarily variable pressing force;
a control section which controls the pressing force applied by the artery pressing section;
a pulse sensor for detecting a pulse of the artery at a pressed point or on a peripheral side thereof; and
a pressure waveform processing section which calculates at least one of the following items based on the pulse waveform obtained by the pulse sensor:
an after-ejection pressure ratio which is a after-ejection pressure normalized by a pulse pressure, the after-ejection pressure being a pressure difference between a dicrotic notch and a maximum blood pressure, the pulse pressure being a difference between the maximum blood pressure and a minimum blood pressure;
a dicrotic notch difference ratio which is a dicrotic notch difference normalized by the pulse pressure, the dicrotic notch difference being a difference between a blood pressure of the dicrotic notch and the minimum blood pressure;
a mean-blood-pressure pulse-pressure ratio which is a ratio of the mean-blood-pressure and the pulse pressure, a dicrotic wave height ratio which is a dicrotic wave height normalized by the pulse pressure; and
a dicrotic-wave-height after-ejection pressure ratio which is a ratio of the dicrotic wave height and the after-ejection pressure.

25. A blood pressure monitor comprising:
a band adapted to be wound around any one of extremities and fingers having a first artery and a second artery;
a pressure applying section which is installed on a inner surface of the band and is adapted to apply a variable pressure to the first artery by changing a volume of a fluid included therein;
a second artery pressing section which is attached to the pressure applying section and is adapted to locally press the second artery;
a control section which controls the pressure applied by the pressure applying section;
a pressure sensor which detects a vibration of the artery transmitted as a pressure change of the fluid via the pressure applying section; and
a blood pressure determination section which determines a maximum blood pressure and a minimum blood pressure based on various pressing force values applied by the pressure applying section and a signal detected by the pressure sensor at each of the pressing force values.

26. A blood pressure monitor comprising:
a band adapted to be wound around any one of extremities and fingers having a first artery and a second artery;
a first artery pressing section which is installed on a inner surface of the band and is adapted to locally apply a variable pressing force to the first artery by changing a volume of a fluid included therein;
a second artery pressing section which is installed on a inner surface of the band and is adapted to locally apply a variable pressing force to the second artery by changing a volume of a fluid included therein;
a control section which controls the pressing force applied by the first artery pressing section;
a pressure sensor which detects a vibration of the artery transmitted as a pressure change of the fluid via the first artery pressing section; and
a blood pressure determination section which determines a maximum blood pressure and a minimum blood pressure based on various pressing force values applied by the first artery pressing section and a signal detected by the pressure sensor at each of the pressing force values.

27. A blood pressure monitor comprising:
an artery pressing section adapted to press an artery of any one of extremities or fingers at an arbitrarily variable pressing force;
a control section which controls the pressing force applied to the artery by the artery pressing section so as to gradually increase the pressing force from a predetermined minimum pressing force;
a pressure sensor detecting a vibration of the artery at a point on the peripheral side of the point to be pressed by the artery pressing section; and
a blood pressure determination section which determines a maximum blood pressure and a minimum blood pressure based on various pressing force values applied by the artery pressing section and a signal detected by the pressure sensor at each of the pressing force values.

28. The blood pressure monitor according to claim 27, further comprising a conversion section which converts a signal detected by the pressure sensor into a blood pressure waveform based on the maximum blood pressure and the minimum blood pressure.

29. The blood pressure monitor according to claim 28, further comprising a blood-pressure-waveform processing section which calculates at least one of following items based on the blood pressure waveform obtained by the conversion section: a mean blood pressure, a pulse pressure which is a difference between the maximum blood pressure and the minimum blood pressure, a after-ejection pressure which is a pressure difference between a dicrotic notch and the maximum blood pressure, a dicrotic wave height which is a pressure difference between the dicrotic notch and a dicrotic wave peak, an after-ejection pressure ratio which is the after-ejection pressure normalized by the pulse pressure, a dicrotic wave height ratio which is the dicrotic wave height normalized by the pulse pressure, and a dicrotic wave height after-ejection pressure ratio which is a ratio of the dicrotic wave height and the after-ejection pressure.

* * * * *